United States Patent
Takehara et al.

(10) Patent No.: US 7,659,409 B2
(45) Date of Patent: Feb. 9, 2010

(54) 3-HYDROXY-3-(2-THIENYL) PROPIONAMIDES AND PRODUCTION METHOD THEREOF, AND PRODUCTION METHOD OF 3-AMINO-1-(2-THIENYL)-1-PROPANOLS USING THE SAME

(75) Inventors: Jun Takehara, Kanagawa (JP); Jingping Qu, Kanagawa (JP); Kazuaki Kanno, Kanagawa (JP); Hiroshi Kawabata, Kanagawa (JP); Yasumasa Dekishima, Kanagawa (JP); Makoto Ueda, Kanagawa (JP); Kyoko Endo, Kanagawa (JP); Takeshi Murakami, Kanagawa (JP); Tomoko Sasaki, Kanagawa (JP); Hisatoshi Uehara, Kanagawa (JP); Youichi Matsumoto, Kanagawa (JP); Shihomi Suzuki, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/944,055

(22) Filed: Sep. 20, 2004

(65) Prior Publication Data

US 2005/0107621 A1    May 19, 2005

Related U.S. Application Data

(63) Continuation of application No. PCT/JP03/03170, filed on Mar. 17, 2003.

(30) Foreign Application Priority Data

| Mar. 19, 2002 | (JP) | P. 2002-076168 |
| Apr. 30, 2002 | (JP) | P. 2002-129140 |
| May 16, 2002 | (JP) | P. 2002-141145 |
| Aug. 5, 2002 | (JP) | P. 2002-227401 |
| Aug. 5, 2002 | (JP) | P. 2002-227402 |
| Aug. 6, 2002 | (JP) | P. 2002-228495 |
| Sep. 13, 2002 | (JP) | P. 2002-267617 |
| Oct. 31, 2002 | (JP) | P. 2002-317857 |

(51) Int. Cl.
 *C07D 333/22* (2006.01)
(52) U.S. Cl. .................................... 549/76
(58) Field of Classification Search .................. 549/76
 See application file for complete search history.

(56) References Cited

U.S. PATENT DOCUMENTS

| 4,956,388 | A | 9/1990 | Robertson et al. | |
| 5,023,269 | A | 6/1991 | Robertson et al. | |
| 5,294,731 | A | 3/1994 | Paust et al. | |
| 6,921,822 | B2 | 7/2005 | Militzer et al. | |
| 2002/0187961 | A1 | 12/2002 | Burk et al. | |
| 2003/0225153 | A1* | 12/2003 | Eckert et al. | 514/438 |
| 2003/0225274 | A1 | 12/2003 | Bosch et al. | |
| 2004/0181058 | A1* | 9/2004 | Berendes et al. | 544/59 |
| 2005/0272940 | A1 | 12/2005 | Houson | |
| 2006/0264641 | A1* | 11/2006 | Berendes et al. | 546/341 |

FOREIGN PATENT DOCUMENTS

| EP | 273658 A1 | 7/1988 |
| EP | 457559 A2 | 11/1991 |
| EP | 562343 A1 | 9/1993 |
| EP | 571685 A1 | 12/1993 |
| EP | 650965 A1 | 5/1995 |
| EP | 0 751 427 | 1/1997 |
| EP | 1 346 977 A1 | 9/2003 |
| JP | 59-163382 A | 9/1984 |
| JP | 63-63398 A | 3/1988 |
| JP | 4-226948 | 8/1992 |
| JP | 06-199747 | 7/1994 |
| JP | 2549681 | 8/1996 |
| JP | 10-168058 | 6/1998 |
| JP | 2000-229946 | 8/2000 |

(Continued)

OTHER PUBLICATIONS

Madec, J. et al, CA:135 : 60899, 2001.*

(Continued)

*Primary Examiner*—Rei-Tsang Shiao
*Assistant Examiner*—Joseph R Kosack
(74) *Attorney, Agent, or Firm*—Oblon, Spivak, McClelland, Maier & Neustadt, L.L.P.

(57) ABSTRACT

The object of the present invention is to provide 3-hydroxy-3-(2-thienyl)propionamides useful as synthesis intermediates of pharmaceutical preparations and the like and a method for obtaining optically active 3-amino-1-(2-thienyl)-1-propanols using the same with high reaction yield, high optical yield and industrially low cost.

According to the present invention, 3-amino-1-(2-thienyl)-1-propanols are obtained by carrying out asymmetric reduction of a β-ketocarbonyl compound having thiophene ring in the presence of a catalyst constituted from a compound of a group VIII or IX metal in the periodic table (e.g., a ruthenium compound) and an asymmetric ligand represented by a specified optically active diamine derivative (e.g., a diphenylethylenediamine derivative), or using a cell, a treated product of said cell or the like of a microorganism, and as occasion demands, carrying out amidation of the ester group and then carrying out reduction of the amido group.

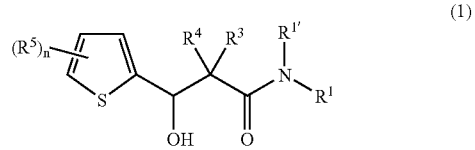

(each of the substituents is as described in claim 1).

7 Claims, 6 Drawing Sheets

FOREIGN PATENT DOCUMENTS

| | | |
|---|---|---|
| JP | 2001-58999 A | 3/2001 |
| JP | 2001-199928 A | 7/2001 |
| JP | 2002-515004 | 5/2002 |
| WO | WO 89/08651 | 9/1989 |
| WO | WO91/16889 A1 | 11/1991 |
| WO | WO 96/01788 | 1/1996 |
| WO | WO 01/89457 | 11/2001 |
| WO | WO 2004/024708 | 3/2004 |

OTHER PUBLICATIONS

Lee, Phil Ho. et al, CA :136: 309728, 2001.*
Miller, Robert E. et al, CA 44 : 22544, 1950.*
Deeter et al. "Asymmetric Synthesis and Absolute Stereochemistry of LY248686" Tetrahedron Letters, 1990, vol. 31, No. 49, pp. 7101-7104.*
Tetrahedron Lett., (1986), 27(43), pp. 5241-5244.
Chem. Pharm. Bull., (1984), 32(4), pp. 1619-1623.
Tetrahedron Lett. (1995), 36(27), pp. 4801-4804.
Tetrahedron, (2001) 57(13), pp. 2563-8.
Virginie Ratovelomanana-Vidal, et al., "Enantioselective ruthenium-mediated hydrogenation: developments and applications", J. Organomet. Chem., vol. 567, 1998, pp. 163-171.
Masahiko Uchiyama, et al., "Highly enantioselective reduction of symmetrical diacetylaromatics with baker's yeast", Tetrahedron: Asymmetry, vol. 8, No. 20, 1997, pp. 3467-3474.
Kaoru Nakamura, et al., "Asymmetric Reduction of Trifluoromethyl Ketones Containing a Sulfur Functionality by the Alcohol Dehydrogenase from Geotrichum", Tetrahedron, vol. 54, 1998, pp. 8393-8402.
Jack Deeter, et al., "Asymmetric Synthesis and Absolute Stereochemistry of LY248686", Tetrahedron Letters, vol. 31, No. 49, 1990, pp. 7101-7104.
Claus Herdeis, et al., "Chiral Pool Synthesis of trans-(2S, 3S)-3-Hydroxyproline and Castanodiol from S-Pyroglutamic Acid", Tetrahedron Asymmetry, vol. 5, No. 1, 1994, pp. 119-128.
Ashok Kumar, et al., "A New Chemoenzymatic Enantioselective Synthesis of R-(-)Tomoxetine, (R)- and (s)-Fluoxetine", Tetrahedron Letters, vol. 32, No. 16. XP-002121769, 1991, pp. 1901-1904.
V. Ratovelomanana-Vidal, et al., "Enantloselective Hydrogenation of β-Keto Esters using Chiral Diphosphine-Ruthenium Complexes: Optimization for Academic and Industrial Purposes and Synthetic Applications", Advanced Synthesis and Catalysis, vol. 345, No. 1-2, XP-002290486, Jan. 21, 2003, pp. 261-274.
Office Action dated Mar. 3, 2009 in corresponding Japanese Application No. 2002-227401. (w/English Translation).
Office Action dated Mar. 10, 2009 in corresponding Japanese Application No. 2002-228495. (w/English Translation).
Office Action dated Mar. 17, 2009 in corresponding Japanese Application No. 2002-317857. (w/English Translation).
Office Action dated Apr. 7, 2009 in corresponding Japanese Application No. 2002-227402. (w/English Translation).
T. Patrick, et al., "Synthesis and Metalation of 2-Ethynylthiophene", Journal of Organic Chemistry, vol. 37, No. 26, 1972, pp. 4467-4468.
M. El-Abadelah, et al., "Synthesis and Properties of 1-Aryl-6-chloro-1,4-dihydro-4-oxothieno[2,3-c]pyridazine-3-carboxylic Acids", Journal Fuer Prakitsche Chemie/Chemiker-Zeitung, vol. 339, No. 3, 1997, pp. 284-287.
"Carbanion-Accelerated Claisen Rearrangements. 4. Asymmetric Induction via 1,3,2-Oxazaphosphorinanes[1a]", Journal of Organic Chemistry, vol. 52, 1987, pp. 5742-5745.
S. Finholt, "Oxidation and Reduction of Organic compounds", Apr. 1, 1964, pp. 765-770.

* cited by examiner

3-HYDROXY-3-(2-THIENYL) PROPIONAMIDES AND PRODUCTION METHOD THEREOF, AND PRODUCTION METHOD OF 3-AMINO-1-(2-THIENYL)-1-PROPANOLS USING THE SAME

This application is a continuation of International application PCT/JP03/03170, filed Mar. 17, 2003.

TECHNICAL FIELD

The present invention relates to optically active γ-hydroxyalkylamines having thiophene ring, illustratively, 3-hydroxy-3-(2-thienyl)propionamides, useful as production intermediates of 3-amino-1-(2-thienyl)-1-propanols and a production method thereof, and a production method of optically active 3-amino-1-(2-thienyl)-1-propanols using the same. An optically active γ-hydroxyalkylamine derivative having a thiophene ring is a substance useful as a physiologically active or pharmacologically active component to be used in pharmaceutical preparations and agricultural chemicals.

BACKGROUND OF THE INVENTION

Regarding the method for producing optically active 3-methylamino-1-(2-thienyl)-1-propanol derivatives, 1) a method in which an N,N-dimethylamino ketone derivative is subjected to asymmetric reduction and then, after protection of the hydroxy group, subjected to de-methylation, like the following reaction scheme (A) described in *Tetrahedron Letters*, p. 7101 (1990) or JP-A-4-226948,

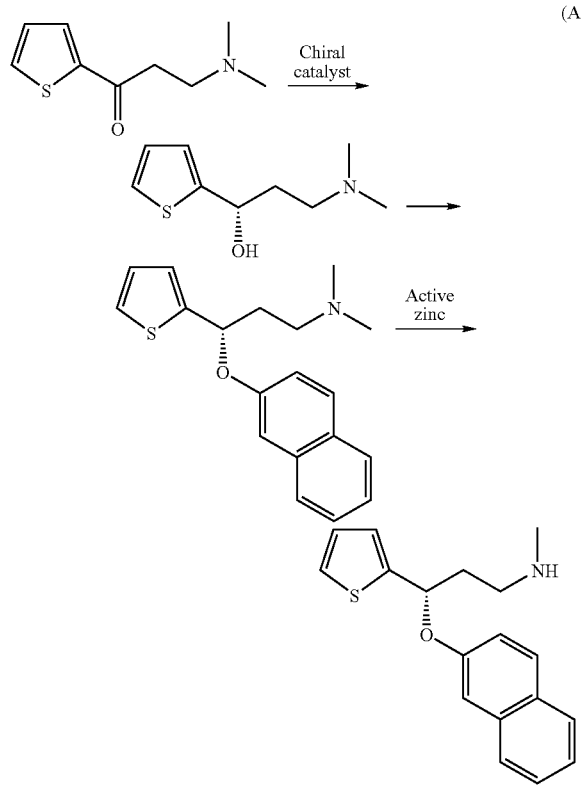

and 2) a method in which an N,N-dimethylaminoalcohol derivative is subjected to optical resolution and then, after protection of the hydroxy group, subjected to de-methylation, like the following reaction scheme (B) described in Japanese Patent No. 2,549,681, are known.

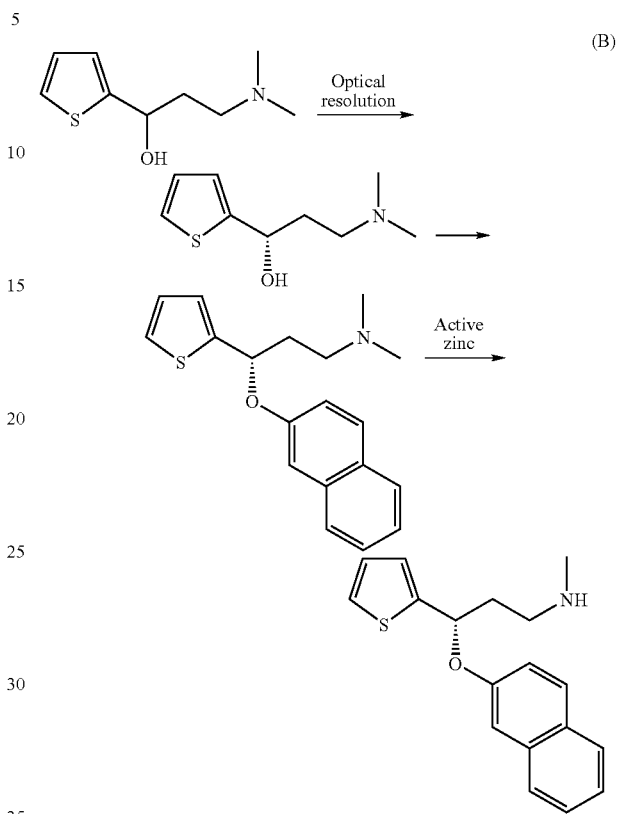

However, the method of 1) requires an expensive optically active ligand and results in a low optical yield of about 85%, and the method of 2) wastes half of the substrate due to the optical resolution. In addition, since active zinc is used in the de-methylation step of both 1) and 2), preparation of the reagent is complicated, removal of metal residue and the like after the reaction is necessary and, what is more, protection of hydroxy group is necessary due to aptness of the free hydroxy group at the α-position of the thiophene ring to cause racemization, and because of these troublesome process and the like problems, concern has been directed toward the development of a more inexpensive and convenient production method.

Also, regarding other method for effecting asymmetric reduction of a β-ketocarbonyl compound having thiophene ring, methods which use an Ru-optically active phosphine complex as the catalyst (*J. Organometallic Chem.*, 567, 163 (1998), *Tetrahedron Lett.*, 36, 4801 (1995), C. R. Acad. Sci. Paris, t. 2, Serie IIc, 175 (1999), *Tetrahedron*, 57, 2563 (2001)) are known, but these have insufficient optical yield and have many unsettled problems in carrying out industrial production.

Also, regarding the method for effecting asymmetric reduction of carbonyl group using a microorganism, various studies have been carried out, but only a method in which 2,5-diacetylthiophene is reduced using baker's yeast (*Tetrahedron Asymmetry* (1997), 8, 3467) and a method in which trifluoromethyl-(2-thienyl) ketone is reduced using *Geotricum candidum* (*Tetrahedron* (1998), 54, 8393) are known as the method for effecting asymmetric reduction of the carbonyl group located at the position adjacent to the thiophene ring, and regarding an optically active 3-hydroxy-3-(2-thienyl)propionic acid ester derivative, its production has been carried out only by a chemical synthesis method which uses an asymmetric catalyst.

Also, as an example which uses an aluminum reducing agent in converting hydroxyalkylamides into hydroxyalkylamines by reducing carbonyl group of the former, a method is known in which a cyclic imide shown in the following reaction scheme (A)

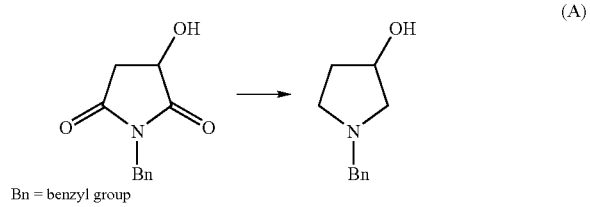

(A)

Bn = benzyl group is reduced using sodium bis(2-methoxyethoxy)aluminum hydride (Red-Al (registered trademark)), the aluminum reducing agent is quenched with a sodium hydroxide aqueous solution after completion of the reaction, and then the target product is obtained by carrying out toluene extraction (cf. JP-A-10-168058).

In addition, as an example which uses a borane reducing agent, a method is known in which a cyclic amide is reduced using a borane-dimethyl sulfide complex and then, after completion of the reaction, 5 M hydrochloric acid aqueous solution is added thereto and heated under reflux in order to decompose the boron-amine complex remained in the reaction mixture, thereby decomposing the complex and isolating the hydroxyalkylamine (*Tetrahedron Asymmetry*, Vol. 5, No. 1, 119 (1994)).

However, when the present inventors have isolated hydroxyalkylamines by the same operation of the former method, it was found that the hydroxyalkylamine as the product is contaminated with a large amount of aluminum originated from the aluminum reducing agent. Since there is a view that aluminum has a possibility of causing Alzheimer disease, it is considered that it is desirable to reduce its contaminating amount as much as possible from a compound to be used as an intermediate of pharmaceutical preparations and agricultural chemicals.

Also, since heat refluxing is carried out using a high concentration hydrohalogenic acid in the latter method, it has a disadvantage in that it cannot be applied to certain substrates having a possibility of causing racemization or dehydration reaction under acidic condition, as well as a possibility of causing corrosion of the reaction vessel, so that this is not desirable industrially. Thus, an industrially useful production method which uses more mild reaction conditions is expected.

The object of the present invention is to provide a method for the industrially convenient and efficient production of optically active γ-hydroxyalkylamines, namely 3-amino-1-(2-thienyl)-1-propanols.

DISCLOSURE OF THE INVENTION

With the aim of solving the aforementioned problems, the inventors have conducted intensive studies and found as a result that 3-hydroxy-3-(2-thienyl)propionamides as novel compounds can be easily produced by asymmetric reduction using a metal catalyst having a specified ligand, or by an asymmetric reduction reaction of carbonyl group using a microbial cell, a treated product of said cell and/or a culture medium, and that optically active 3-amino-1-(2-thienyl)-1-propanols can be industrially obtained from said amides by further subjecting to a carbonyl group reduction reaction, thus resulting in the accomplishment of the present invention.

Accordingly, the gist of the present invention is as follows.

1, A 3-hydroxy-3-(2-thienyl)propionamide represented by the following general formula (1)

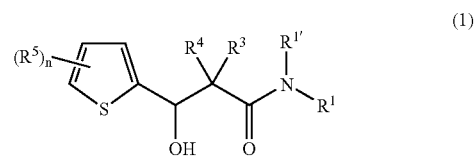

(1)

(wherein $R^1$ and $R^{1'}$ each independently represents a hydrogen atom, an alkyl group, an aryl group or an aralkyl group, $R^3$ and $R^4$ each independently represents a hydrogen atom or an alkyl group (wherein $R^3$ and $R^4$ may together form a carbon ring), $R^5$ represents a halogen atom, a nitro group, a hydroxyl group, an alkyl group which may be substituted, an aryl group which may be substituted or an alkoxy group which may be substituted, and n is an integer of from 0 to 3).

2, A method for producing the aforementioned 3-hydroxy-3-(2-thienyl)propionamide, characterized in that a β-ketocarbonyl compound represented by the following general formula (1')

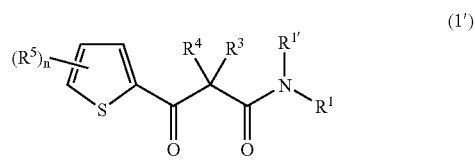

(1')

(wherein $R^1$, $R^{1'}$, $R^3$, $R^4$, $R^5$ and n are as defined in the foregoing) is subjected to an asymmetric reduction in the presence of a catalyst constituted from a compound of a group VIII or IX metal in the periodic table and an asymmetric ligand represented by the following general formula (2)

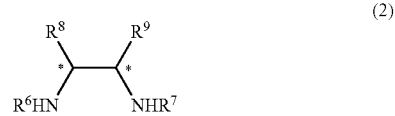

(2)

(wherein $R^6$ and $R^7$ each independently represents a hydrogen atom, an alkyl group, an acyl group, a carbamoyl group, a thioacyl group, a thiocarbamoyl group, an alkylsulfonyl group or an arylsulfonyl group, $R^8$ and $R^9$ each independently represents an alkyl group which may have substituent(s), an aryl group which may have substituent(s) or a heteroaryl group which may have substituent(s), wherein $R^8$ and $R^9$ may be boned to each other to form a ring, and * represents an asymmetric carbon), or a β-ketocarbonyl compound represented by the following general formula (3)

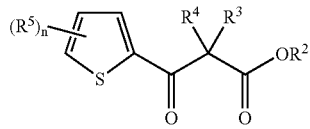
(3)

(wherein $R^2$ represents an alkyl group, an aryl group or an aralkyl group, and $R^3$, $R^4$, $R^5$ and n are as defined in the foregoing) is subjected to an asymmetric reduction in the presence of a catalyst constituted from a compound of a group VIII or IX metal in the periodic table and an asymmetric ligand represented by the following general formula (2)

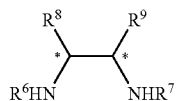
(2)

(wherein $R^6$ and $R^7$ each independently represents a hydrogen atom, an alkyl group, an acyl group, a carbamoyl group, a thioacyl group, a thiocarbamoyl group, an alkylsulfonyl group or an arylsulfonyl group, $R^8$ and $R^9$ each independently represents an alkyl group which may have substituent(s), an aryl group which may have substituent(s) or a heteroaryl group which may have substituent(s), wherein $R^8$ and $R^9$ may be boned to each other to form a ring, and * represents an asymmetric carbon), or using a cell, a treated product of said cell and/or a culture medium of a microorganism, and then the resulting product is allowed to react with amines represented by $R^1R^{1'}NH(R^1$ and $R^{1'}$ are as defined in the foregoing) to effect its amidation.

3, An optically active 3-hydroxy-3-(2-thienyl)propionic acid ester compound represented by the following general formula (3')

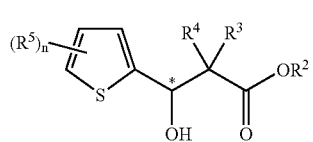
(3')

(wherein $R^2$, $R^3$, $R^4$, $R^5$ and n are as defined in the foregoing, and * represents an asymmetric carbon).

4, A method for producing optically active 3-amino-1-(2-thienyl)-1-propanols by reducing the carbonyl group of the aforementioned 3-hydroxy-3-(2-thienyl)propionamide, characterized in that the treatment after completion of the reduction reaction is carried out at a pH of 4 or more.

5, A 3-amino-1-(2-thienyl)-1-propanol, characterized in that the impurity aluminum content is within the range of from 0.001 ppm to 500 ppm.

6, A method for producing an optically active 3-amino-1-(2-thienyl)-1-propanol derivative, characterized in that optically active 3-amino-1-(2-thienyl)-1-propanols are further subjected to a hydroxyl group protecting reaction.

BEST MODE FOR CARRYING OUT THE INVENTION

Figure 1:
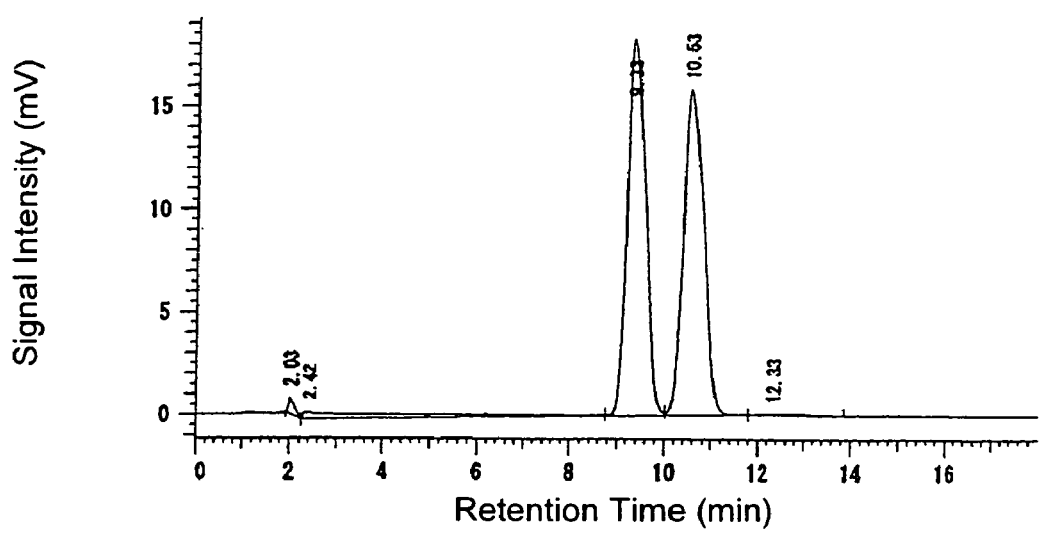
FIG. 1 is a chart showing a result of the HPLC analysis of racemic bodies of 3-hydroxy-3-(2-thienyl)propionic acid ethyl ester. The retention time (minute) is plotted as abscissa, and the signal strength (mV) as ordinate.

The following describes the present invention in detail.

A) 3-Hydroxy-3-(2-thienyl)propionamide

The 3-hydroxy-3-(2-thienyl)propionamide of the present invention is a novel compound, and an optically active 3-amino-1-(2-thienyl)-1-propanol derivative useful as a physiologically active or pharmacologically active component that can be used in pharmaceutical preparations and agricultural chemicals can be conveniently produced from said compound.

As the 3-hydroxy-3-(2-thienyl)propionamide of the present invention, those having a molecular weight of generally 1,000 or less, preferably 750 or less, and more preferably 500 or less, can be cited, In the aforementioned general formula (1), $R^1$ and $R^{1'}$ each independently represents hydrogen atom; methyl group, ethyl group, n-propyl group, isopropyl group, cyclopropyl group, n-butyl group, isobutyl group, tertiary butyl group, n-pentyl group, isopentyl group, neopentyl group, tertiary pentyl group, isoamyl group, n-hexyl group or the like straight chain, branched chain or cyclic alkyl group having from 1 to 8 carbon atoms; phenyl group, mesityl group, naphthyl group or the like aryl group; or benzyl group, phenethyl group, naphthylmethyl group, diphenylmethyl group or the like aralkyl group. Preferred as the alkyl group among them is an alkyl group having from 1 to 6, more preferably from 1 to 4, carbon atoms, and is further preferably methyl group or ethyl group, preferred as the aryl group is an aryl group having from 6 to 10 carbon atoms, more preferably phenyl group, and preferred as the aralkyl group is a group having from 7 to 16 carbon atoms, more preferably benzyl group.

Particularly, a case in which either one of $R^1$ and $R^{1'}$ is hydrogen atom and the other is an alkyl group having from 1 to 4 carbon atoms, phenyl group or benzyl group is desirable, and a case in which either one of $R^1$ and $R^{1'}$ is hydrogen atom and the other is an alkyl group having from 1 to 4 carbon atoms is more desirable.

$R^3$ and $R^4$ each independently represents hydrogen atom or an alkyl group. As the alkyl group, the same groups cited in the description on the aforementioned $R^1$ and $R^{1'}$ can be exemplified. In addition, $R^3$ and $R^4$ may together form ethylene group or propylene group, 1,3-dimethylpropylene group, tetramethylene group, pentamethylene group or the like, and may form a carbon ring together with the carbon atoms to which these groups are bonded. Preferred among them is hydrogen atom or an alkyl group having from 1 to 4 carbon atoms, more preferred is a case in which either one of $R^3$ and $R^4$ is hydrogen atom, particularly preferred is a case in which both of $R^3$ and $R^4$ are hydrogen atoms.

$R^5$ is fluorine atom, chlorine atom, bromine atom or the like halogen atom; nitro group; hydroxyl group; an alkyl group which may be substituted; an aryl group which may be substituted; or an alkoxy group which may be substituted.

In this case, as these alkyl group and aryl group, the same groups cited in the description on the aforementioned $R^1$ and $R^{1'}$ can be exemplified, and examples of the alkoxy group described in the above include methoxy group, ethoxy group, n-propoxy group, isopropoxy group, n-butoxy group, isobutoxy group, tertiary butoxy group and the like straight or branched-chain alkoxy groups, preferably alkoxy groups having from 1 to 6 carbon atoms, more preferably from 1 to 4 carbon atoms.

In addition, the substituent of the aforementioned alkyl group, aryl group and alkoxy group is not particularly limited with the proviso that it is a group which does not exert a bad influence upon the reaction, and its illustrative examples include an alkyl group, an aryl group, an alkoxy group, a halogen group, cyano group, amino group, nitro group, hydroxyl group and the like.

Among them, the aforementioned $R^5$ is preferably a halogen atom, an alkyl group which may be substituted, an aryl group which may be substituted or an alkoxy group which may be substituted, more preferably a halogen atom, an alkyl group having from 1 to 4 carbon atoms or an alkoxy group having from 1 to 4 carbon atoms, further preferably a halogen atom or an alkyl group having from 1 to 4 carbon atoms.

The symbol n is an integer of from 0 to 3, preferably 0 or 1, and its substitution position is preferably the α-position of sulfur atom of the thiophene ring, particularly preferably 0.

B) Production Method of
3-hydroxy-3-(2-thienyl)propionamide

The aforementioned 3-hydroxy-3-(2-thienyl)propionamide can be produced by either 1) a method in which a β-ketocarbonyl compound represented by the aforementioned general formula (1') is subjected to an asymmetric reduction in the presence of a catalyst constituted from a compound of a group VIII or IX metal in the periodic table and an asymmetric ligand represented by the aforementioned general formula (2), or 2) a method in which a β-ketocarbonyl compound represented by the aforementioned general formula (3) is subjected to an asymmetric reduction in the presence of a catalyst constituted from a compound of a group VIII or IX metal in the periodic table and an asymmetric ligand represented by the aforementioned general formula (2), or using a cell, a treated product of said cell and/or a culture medium of a microorganism having the ability to stereoselectively reduce carbonyl group, and then the resulting product is allowed to react with amines represented by $R^1R^{1'}NH$ ($R^1$ and $R^{1'}$ are as defined in the foregoing).

In this case, the compound represented by the aforementioned general formula (1') is a compound in which the group bonded to the thiophene ring is carbonyl group, and is converted into the compound of general formula (1) by the asymmetric reduction of said carbonyl group.

Also, the compound represented by the aforementioned formula (3) is a compound in which the group bonded to the thiophene ring is carbonyl group and the terminus is a carboxylate group. This is converted into the compound of general formula (1) by allowing said carbonyl group to undergo asymmetric reduction and to react with amines, and converting the terminal carboxylate group into amido group.

In the aforementioned general formula (1') and general formula (3), $R^1$, $R^{1'}$, $R^3$, $R^4$, $R^5$ and n are as defined in the foregoing, and $R^2$ represents an alkyl group, an aryl group or an aralkyl group. In this case, the same groups exemplified in the description of $R^1$ and $R^{1'}$ can be cited as the alkyl group, aryl group and aralkyl group of $R^3$.

In addition, the compound represented by the aforementioned general formula (1') can be produced by carrying out amidation of the compound represented by the aforementioned general formula (3). On the other hand, the compound represented by the aforementioned general formula (3) can be produced by a conventionally known method such as a reaction of acetylthiophenes with carbonic esters, but in a method desirably employed, a carbonic ester and a base are allowed to contact with each other in advance at a temperature of about 35° C. or less, preferably within the range of from 0° C. to 35° C., and then, after increasing the temperature to 40° C. or more, preferably 50° C. or more as occasion demands, an acetylthiophene is added thereto.

In the following, preferred production method of the compound represented by the general formula (3) is described in detail.

(Production Method of the Compound Represented by the General Formula (3))

Regarding the carbonic esters to be used in the aforementioned reaction, they may be optionally used in response to the compound represented by the aforementioned general formula (3), but preferably, dialkylcarbonates having from 1 to 6 carbon atoms can be exemplified, and they are used within the range of from 2 mol 10 mol equivalent, preferably within the range of from 2.5 mol 8 mol equivalent, based on the acetylthiophenes.

The base to be used in the aforementioned reaction is not particularly limited, with the proviso that it has the ability to generate anion at the α-position of carbonyl group, and its illustrative examples include metallic sodium, metallic potassium and the like alkali metals; sodium hydroxide, potassium hydroxide and the like alkali metal hydroxides; sodium amide, potassium amide and the like alkali metal amides; lithium hydride, potassium hydride, sodium hydride and the like alkali metal hydrides; and sodium methoxide, sodium ethoxide, sodium tert-butoxide, potassium tert-butoxide and the like alkali metal alkoxides. Preferred among them is an alkali metal hydride or an alkali metal alkoxide, and more preferred is sodium hydride, sodium tert-butoxide or potassium tert-butoxide. In this connection, regarding the aforementioned alkali metal hydrides, those which are generally on the market and contain oil components can be used as such. Regarding the amount of said base to be used, theoretically equivalent mol or more is used in general, based on acetylthiophenes, of which an excess amount is desirable. However, since too large amount of the base is not desirable in view of its effect and cost, it is used generally within the range of approximately 5 moles or less, preferably about 3 moles or less.

The reaction is carried out at a temperature of 40° C. or more, preferably 50° C. or more, as described in the foregoing and, though it depends on the solvent to be used, can be carried out under refluxing condition. However, since too high reaction temperature causes a problem of causing degradation of the target substance, the reaction is carried out generally within the range of 110° C. or less.

In this reaction, a solvent is generally used from the agitation efficiency and the like points of view. The solvent to be used is not particularly limited with the proviso that it does not inactivate the base, and its illustrative examples include diethyl ether, tetrahydrofuran and the like ether solvents; or toluene, xylene and the like aromatic solvents, of which ether solvents are preferred, and tetrahydrofuran is particularly preferred.

Though it depends on the reaction scale, the solvent is used within the range of generally 1 volume or more, preferably 2 volumes or more, more preferably 3 volumes or more, based on the substrate. However, since too large amount of the solvent causes a problem in terms of pot efficiency, it is used within the range of generally 100 volumes or less, preferably 20 volumes or less, more preferably 10 volumes or less.

In addition, though it depends on the equilibrium between reaction scale and adding rate, the acetylthiophenes may be added by dissolving in a solvent. Amount of the solvent is generally from about 0.2 to about 5 volumes, preferably from about 0.5 to about About 3 volumes, based on the acetylthiophenes.

The reaction is carried out by stirring for 30 minutes or more after completion of the addition of acetylthiophene and, though it depends on the reaction scale, completed generally after a few hours.

After completion of the reaction, the reaction solution is added to water in order to treat unreacted base and thereby to terminate the reaction. In that case, in order to prevent hydrolysis and the like of the product, it is desirable to control pH of the treating solution within the range of from 5 to 8, more preferably from about 6 to about 7.

General isolation purification methods may be carried out in isolating the compound represented by the general formula (3) after the aforementioned reaction termination; illustratively, it can be isolated after extracting the treated solution after termination of the reaction with toluene or the like organic solvent, concentrating the thus obtained organic layer and then purifying it using distillation, column chromatography and the like general purification techniques.

(Amidation of Compound Represented by the General Formula (3))

The compound represented by the general formula (3) obtained by the aforementioned method can be converted into the compound represented by the aforementioned general formula (1') by allowing it to react with amines represented by $R^1R^{1'}NH$ ($R^1$ and $R^{1'}$ are as defined in the foregoing) to effect its amidation.

The amidation reaction described in the above may be carried out in accordance with a general conventionally known amidation method of esters with amines. Illustratively, the amidation reaction can be carried out by allowing an ester and an amine to react with each other.

The amount of amines to be used may be 1 equivalent or more, preferably 2 equivalents or more, based on esters. Since too large using amount causes a difficulty in removing excess amines after completion of the reaction in some cases, they are used within the range of generally 30 equivalents or less, preferably 15 equivalents or less, particularly preferably 10 equivalents or less, further preferably 5 equivalents or less, based on esters.

Though the reaction can be carried out without solvent when the substrate or substrate mixture is liquid, a liquid solvent may be used as occasion demands and such a solvent to be used is not particularly limited with the proviso that it does not inactivate the reaction substrate, and its illustrative examples include diethyl ether, tetrahydrofuran and the like ether solvents; toluene, xylene and the like aromatic solvents; pentane, hexane, heptane and the like aliphatic hydrocarbons; methylene chloride, chloroform and the like halogen solvents; methanol, ethanol and the like alcohol solvents; and N,N-dimethylformamide, dimethyl sulfoxide, N-methylpyrrolidone and the like aprotic polar solvents.

The reaction temperature is optionally set within the range of generally −20° C. or more, preferably 0° C. or more, more preferably 10° C. or more, but it is desirable carry out the reaction within the range of generally 200° C. or less, preferably boiling point or less of the solvent.

It is desirable to exclude by-producing alcohol from the system for the purpose of improving the reaction rate.

After carrying out the reaction for a predetermined period of time, the thus formed amides represented by the general formula (1') can be obtained by removing the by-produced alcohol and excess amines through distillation or the like concentration operation. The thus obtained amides can be purified by a combination of a chromatographic purification, crystallization and the like general purification techniques.

As the method for carrying out asymmetric reduction of the compound represented by the general formula (3) or the compound represented by the general formula (1') obtained by the aforementioned method, an asymmetric reduction which uses an asymmetric catalyst and an asymmetric reduction that uses a microorganism are respectively described in the following.

B-1) Asymmetric Reduction which Uses an Asymmetric Catalyst (Asymmetric Catalyst)

The asymmetric catalyst to be used in the asymmetric reduction of the present invention is a catalyst formed from a compound of a group VIII or group IX metal in the periodic table and a compound represented by the aforementioned general formula (2).

As the compound of a group VIII or group IX metal in the periodic table, halides of ruthenium, rhodium, iridium, cobalt and the like, olefin complexes, arene complexes, carbonyl complexes and the like can be exemplified, of which a ruthenium compound is desirable. Illustrative examples of said compound include $RuCl_3\cdot 3H_2O$, $[RuCl_2(p\text{-cymene})]_2$, $[RuCl_2(benzene)]_2$, $[RuCl(mesytilene)]_2$, $[RuCl(hexamethylbenzene)]_2$, $RuCl_2(PPh_3)_3$, $[RuCl_2(cod)]_n$, $[RuCl_2(CO)_3]_2$, $[Rh(cod)Cl]_2$, $[RhCl_2(pentamethylcyclopentadienyl)]_2$, $[Ir(cod)Cl]_2$, $CoCl_2$ and the like, of which $[RuCl_2(p\text{-cymene})]_2$ is particularly desirable. In this connection, Ph in the above compounds represents phenyl group, and cod indicates cyclooctadiene.

In the compound represented by the aforementioned general formula (2), $R^6$ and $R^7$ are each independently hydrogen atom; methyl group, ethyl group, n-propyl group, i-propyl group, n-butyl group or the like alkyl group; acetyl group, propionyl group, benzoyl group or the like acyl group; N-methylcarbamoyl group, N-phenylcarbamoyl group or the like carbamoyl group; thioacetyl group, thiopropionyl group, thiobenzoyl group or the like thioacyl group; or N-methylthiocarbamoyl group, N-phenylthiocarbamoyl group or the like thiocarbamoyl group; methylsulfonyl group, ethylsulfonyl group, chloromethylsulfonyl group, methoxymethylsulfonyl group or the like alkylsulfonyl group or, as an arylsulfonyl group, phenylsulfonyl group, tolylsulfonyl group, 4-methoxyphenylsulfonyl group, 4-chlorophenylsulfonyl group, 2-naphthylsulfonyl group or the like arylsulfonyl group. Preferred as the aforementioned alkyl group, acyl group, carbamoyl group, thioacyl group and thiocarbamoyl group are those which have 8 or less, more preferably 4 or less, of carbon atoms, and preferred as the alkylsulfonyl group and arylsulfonyl group are those which have 20 or less of carbon atoms.

Preferred among them is a compound represented by the general formula (2'), that is, a case in which either one of $R^6$ and $R^7$ is an alkylsulfonyl group or an arylsulfonyl group is desirable, a case in which either one of $R^6$ and $R^7$ is arylsulfonyl is more desirable, and a case in which either one of $R^6$ and $R^7$ is tolylsulfonyl group is particularly desirable.

In this connection, $R^{10}$ in the compound represented by the general formula (2') is an alkyl group which may have substituent(s) or an aryl group which may have substituent(s). Examples of the alkyl group described in the above include methyl group, ethyl group, n-propyl group, i-propyl group, n-butyl group, n-pentyl group, n-hexyl group and the like having from 1 to 20 carbon atoms, and examples of the aryl group include phenyl group, naphthyl group and the like having from 6 to 20 carbon atoms. Illustrative examples of the substituent of such alkyl groups and aryl groups include methyl group, ethyl group, n-propyl group, i-propyl group, n-butyl group and the like lower alkyl groups having from 1 to 4 carbon atoms; fluorine atom, chlorine atom, bromine atom and the like halogen atoms; and methoxy group, ethoxy group, n-propoxy group, i-propoxy group and the like lower alkoxy groups having from 1 to 4 carbon atoms.

In the compound represented by the aforementioned general formula (2), $R^8$ and $R^9$ are each independently an alkyl group which may have substituent(s), an aryl group which may have substituent(s) or a heteroaryl group which may have substituent(s). Examples of the alkyl group described in the above include methyl group, ethyl group, n-propyl group, i-propyl group and the like having from 1 to 6 carbon atoms, examples of the aryl group include phenyl group, 4-methylphenyl group, 3,5-dimethylphenyl group, naphthyl group and the like having from 6 to 12 carbon atoms, and examples of the heteroaryl group include furyl group, pyridyl group and the like 5- to 6-membered ring groups containing nitrogen atom, oxygen atom, sulfur atom and the like. In addition, $R^8$ and $R^9$ can jointly form, together with the carbon atoms to which they are bonded, cyclohexane ring, cyclopentane ring or the like carbon ring or tetrahydrofuran ring, pyrrolidine ring, tetrahydrothiophene ring or the like heterocyclic ring containing oxygen, nitrogen, sulfur or the like hetero atom in the ring. These groups may further have substituent(s), and such a substituent include methyl group, ethyl group, propyl group and the like lower alkyl groups having from 1 to 4 carbon atoms; methoxy group, ethoxy group and the like lower alkoxy group having from 1 to 4 carbon atoms; and 1 or 2 or more groups selected from chlorine atom, bromine atom, fluorine atom and the like halogen atoms. Among them, phenyl group which may be substituted is desirable as $R^8$ and $R^9$.

Illustrative examples of the asymmetric ligand represented by the aforementioned general formula (2) include 1,2-diphenylethylenediamine, N-methyl-1,2-diphenylethylenediamine, N-tosyl-1,2-diphenylethylenediamine, N-methyl-N'-tosyl-1,2-diphenylethylenediamine, N-p-methoxyphenylsulfonyl-1,2-diphenylethylenediamine, N-p-chlorophenylsulfonyl-1,2-diphenylethylenediamine, N-p-mesitylsulfonyl-1,2-diphenylethylenediamine, N-(2,4,6-tri-i-propyl)phenylsulfonyl-1,2-diphenylethylenediamine and the like.

Regarding formation of the catalyst from an asymmetric ligand represented by the general formula (2) and a metal compound, a conventionally known method disclosed in *J. Am. Chem. Soc.*, 1995, 117, p. 7562, or the like and a method in which a complex is used by isolating as crystals as described in *Angew. Chem. Int. Ed. Engl.*, 1997, 36, p. 285, can be employed.

In the case of a method in which the catalyst is prepared and isolated in advance, the aforementioned metal compound and asymmetric ligand are allowed to react with each other in a solvent prior to the asymmetric reduction reaction, and the thus formed catalyst is isolated.

The solvent to be used in this case is not particularly limited with the proviso that it does not exert influence upon the reaction, and diethyl ether, tetrahydrofuran and the like ether solvents; methanol, ethanol, 2-propanol and the like alcohols; benzene, toluene and the like aromatic hydrocarbons; and acetonitrile, N,N-dimethylformamide and the like aprotic polar solvents are desirable, of which 2-propanol is particularly desirable.

The reaction of an asymmetric ligand with a metal compound is theoretically an equivalent molar reaction, but it is desirable to use the asymmetric ligand in an equivalent molar amount or more based on the metal compound in view of the catalyst preparation rate. Particularly, when [RuCl$_2$(p-cymene)]$_2$ is used as the ruthenium compound and a compound (2) (wherein $R^6$ and $R^7$ each independently represents a hydrogen atom, an alkyl group, an alkylsulfonyl group or an arylsulfonyl group, $R^8$ and $R^9$ each independently represents an aryl group which may have substituent(s), and * represents an asymmetric carbon) is used as the asymmetric ligand, preparation of the catalyst quickly progresses at the equivalent molar ratio, which is desirable.

In addition, in the case of a catalyst in which Y is a halogen atom, it is desirable to allow a base to coexist at the time of the preparation. Examples of the base in this case include trimethylamine, triethylamine, triisopropylamine and the like tertiary organic amines; LiOH, NaOH, KOH, K$_2$CO$_3$ and the like inorganic bases; and sodium methoxide, potassium methoxide and the like metal alkoxides, of which tertiary organic amines are desirable, and triethylamine is particularly suitable. Amount of the base to be added is equivalent mol or more based on the metal atom.

The reaction is carried out generally at a temperature of 0° C. or more and refluxing temperature or less, and a higher reaction temperature is desirable because preparation rate of the catalyst becomes quick. However, since too high temperature causes degradation of the catalyst in some cases, this is carried out generally at 120° C. or less, preferably at 100° C. or less.

In addition, when the metal compound and asymmetric ligand are mixed in the presence of a solvent, the mixture generally forms a state of slurry in many cases and changes to a state of liquid as the formation of catalyst advances, so that completion of the reaction can also be confirmed by this.

After completion of the reaction, the catalyst of interest can be separated by a general crystallization technique such as concentration of the reaction solution or addition of a bad solvent. Also, in case that a hydrohalogenic acid salt is by-produced during the aforementioned preparation, an operation of washing with water may be carried out as occasion demands.

In addition, when preparation of catalyst is simultaneously carried out in an asymmetric reduction reaction system, a method in which the aforementioned ruthenium compound and asymmetric ligand are allowed to contact with each other in the coexistence of a hydrogen donor and then a reducing substrate is added thereto and a method in which the ruthenium compound, asymmetric ligand and reducing substrate are added at the same time can be exemplified. In either of these cases, ratio of the using amounts of ruthenium compound and asymmetric ligand and the like are as described in the foregoing. In addition, reaction conditions such as reaction solvent and temperature may be employed in accordance with the asymmetric reduction reaction conditions which are described later.

As the catalyst to be formed from the aforementioned ligand and metal compound in this manner, those which are represented by the aforementioned general formula (4) are used particularly suitably.

In the aforementioned general formula (4), $R^6$, $R^7$, $R^8$ and $R^9$ are as defined in the foregoing, Y represents hydrogen atom or a halogen atom, and Ar represents an aryl group which may have substituent(s). As the aryl group which may have substituent(s) of Ar of this case, phenyl group, naphthyl group and the like having from 6 to 20 carbon atoms can be exemplified, which may have methyl group, ethyl group, n-propyl group, i-propyl group, n-butyl group or the like alkyl group having from 1 to 4 carbon atoms; fluorine atom, chlorine atom, bromine atom or the like halogen atom; or methoxy group, ethoxy group, n-propoxy group, i-propoxy group or the like alkoxy group having from 1 to 4 carbon atoms, on the ring.

In this connection, when Y is a halogen atom, the compound represented by the aforementioned general formula (4) can be converted easily into its counterpart in which Y is hydrogen atom, by allowing the former to contact with a hydrogen donor under a basic condition. As the hydrogen donor in this case, borohydride compounds and the like metal hydrides and those which are generally used as the hydrogen donor in the hydrogen transfer type reduction reaction, such as formic acid, 2-propanol and the like, are used in the same manner, and their amount to be used may be equivalent mol or more calculated as hydride, based on the catalyst. Also, examples of the base to be used for obtaining the basic condition include trimethylamine, triethylamine, triisopropylamine and the like tertiary organic amines; LiOH, NaOH, KOH, $K_2CO_3$ and the like inorganic bases; and sodium methoxide, potassium methoxide and the like metal alkoxides. In addition, conversion of the compound in which Y is a halogen atom into its counterpart in which it is hydrogen atom may be carried out in advance before subjecting to the asymmetric reduction reaction or in the asymmetric reduction reaction system.

(Asymmetric Reduction Reaction)

In the asymmetric reduction reaction of the present invention, the catalyst obtained by the aforementioned method is allowed to react upon a β-ketocarbonyl compound represented by the aforementioned general formula (1') or (3) in the coexistence of a hydrogen donor. Said hydrogen donor is not particularly limited with the proviso that it is used in the general hydrogen transfer type reduction reaction, such as formic acid, 2-propanol or the like.

In addition, it is desirable to carry out the asymmetric reduction reaction in the presence of a base. When a base is present, the catalyst is stabilized and activity reduction and the like by impurities can be prevented. Examples of the base include trimethylamine, triethylamine, triisopropylamine and the like tertiary organic amines and LiOH, NaOH, KOH, $K_2CO_3$ and the like inorganic bases. Suitable base is triethylamine. The base is used in an excess amount based on the catalyst, e.g., from 1 to 10,000 times by molar ratio. When triethylamine is used, it is desirable to use it in an amount of from 1 to 1,000 times based on the catalyst.

Among combinations of the aforementioned hydrogen donors with bases, it is desirable to use an amine as the base when the hydrogen donor is formic acid, and in that case, the formic acid and amine may be separately added to the reaction system but it is desirable to use the formic acid and amine by making them into an azeotropic mixture in advance, because influences of impurities in these materials can be controlled.

In the reaction, formic acid or 2-propanol as the hydrogen donor is generally used as the reaction solvent, but in order to dissolve the materials, it is possible to use toluene, tetrahydrofuran, acetonitrile, dimethylformamide, dimethyl sulfoxide and the like non-hydrogen donative solvents as assisting solvents, alone or as a mixture. Acetonitrile or dimethylformamide is particularly desirable, because the reaction rate is increased when this is used as the solvent.

Using amount of the catalyst is selected within the range of from 10 to 1,000,000, preferably from 100 to 5,000, as molar ratio (S/C) of the substrate (a β-ketocarbonyl compound represented by the aforementioned formula (1)) to the metal atom of the catalyst.

Regarding the amount of the hydrogen donor based on the β-ketocarbonyl compound represented by the aforementioned general formula (1') or (3), equivalent mole or more is generally used, and when the hydrogen donor is formic acid, 1.5 moles or more is desirable, and used within the range of 20 moles or less, preferably 10 moles or less. On the other hand, when the hydrogen donor is isopropanol, it is used in large excess based on the substrate from the viewpoint of reaction equilibrium and used generally within the range of 1,000 moles or less.

The reaction temperature is selected within the range of from −70 to 100° C., preferably from 0 to 70° C.

The reaction pressure is not particularly limited, and the reaction is carried out generally under 0.5 to 2 atmospheric pressure, preferably under ordinary pressure.

The reaction time is from 1 to 100 hours, generally from 2 to 50 hours.

After the reaction, the thus formed optically active alcohol can be separated and purified from the reaction solution by distillation, extraction, chromatography, recrystallization and the like general operations.

B-2) Asymmetric Reduction Using Microorganism

Asymmetric reduction of the β-ketocarbonyl compound represented by the aforementioned general formula (3) can also be effected using cells of a microorganism having the ability to stereoselectively reduce carbonyl group, a treated product of said cells and/or a culture medium.

(Microorganisms)

The microorganism which can be used in the present invention is not particularly limited, with the proviso that it has the ability to stereoselectively reduce the carbonyl group of 3-oxo-3-(2-thienyl)propionic acid ester derivatives (to be referred this sometimes to as "stereoselective reduction activity" hereinafter). Regarding the method for verifying stereoselective reduction activity, generally a microorganism to be used, a treated product of its cells or a culture medium is allowed to react with an aqueous solution containing the β-ketocarbonyl compound represented by the aforementioned general formula (3), and the aforementioned substrate and the formed product 3-hydroxy-3-(2-thienyl)propionic acid ester derivative in the resulting reaction solution are detected and determined using a thin layer chromatography, a gas chromatography or a liquid chromatography.

The microorganism which can be used in the present invention is a strain having such an activity that decrease in the material substrate can be confirmed when it is subjected to the aforementioned method for verifying stereoselective reduction activity and allowed undergo the reaction for a few hours or more, preferably 1 day or more, illustratively, a strain by which 1% or more, preferably 5% or more, of the material substrate is reduced when allowed to undergo the reaction for a few hours or more, preferably 1 day or more.

Examples of the microorganism which has the ability to produce R-form 3-hydroxy-3-(2-thienyl)propionic acid ester derivatives by stereoselectively reducing the β-ketocarbonyl compound represented by the aforementioned general formula (3) include microorganisms belonging to the genus *Arthrobacter*, the genus *Candida*, the genus *Ctyptococcus*, the genus *Kloeckela*, the genus *Kodamaea*, the genus *Leucosporidium*, the genus *Metschnikowia*, the genus *Paenibacillus*, the genus *Pichia* and the genus *Saccharomyces*.

Examples of the microorganism belonging to the genus *Arthrobacter* preferably include *Arthrobacter atrocyaneus* such as *Arthrobacter atrocyaneus* JCM 1329 and the like.

Examples of the microorganism belonging to the genus *Candida* preferably include *Candida albicans* such as *Candida albicans* IFO 0759 and the like, *Candida holmii* such as *Candida holmii* IFO 1629 and the like, *Candida parapsilosis* such as *Candida parapsilosis* IFO 1396, *Candida parapsilosis* CBS 604 and the like, *Candida vaccinii* such as *Candida vaccinii* JCM 9446 and the like and *Candida valida* such as *Candida valida* IFO 10318 and the like.

Preferred examples of the microorganism belonging to the genus *Cryptococcus* include *Cryptococcus humicolus* such as *Cryptococcus humicolus* IFO 10250 and the like.

Preferred examples of the microorganism belonging to the genus *Kloeckela* include *Kloeckela cortices* such as *Kloeckela cortices* IFO 0631, *Kloeckela cortices* IFO 10318 and the like.

Preferred examples of the microorganism belonging to the genus *Kodamaea* include *Kodamaea ohmeri* such as *Kodamaea ohmeri* IFO 0158 and the like.

Preferred examples of the microorganism belonging to the genus *Leucosporidium* include *Leucosporidium scottii* such as *Leucosporidium scottii* IFO 1212 and the like.

Preferred examples of the microorganism belonging to the genus *Metschnikowia* include *Metschnikowia bicuspidate* such as *Metschnikowia bicuspidate* var. *california* IFO 10787 and the like, *Metschnikowia krissii* such as *Metschnikowia krissii* IFO 1677 and the like, and *Metschnikowia pulcherrima* such as *Metschnikowia pulcherrima* IAM 12197, *Metschnikowia pulcherrima* IAM 12197, *Metschnikowia pulcherrima* IFO 0863, *Metschnikowia pulcherrima* IFO 10796, *Metschnikowia pulcherrima* IFO 1407, *Metschnikowia pulcherrima* IFO 1678 and the like.

Preferred examples of the microorganism belonging to the genus *Paenibacillus* include *Paenibacillus alvei* such as *Paenibacillus alvei* IFO 3343 and the like.

Preferred examples of the microorganism belonging to the genus *Pichia* include *Pichia angophorae* such as *Pichia angophorae* IFO 10016 and the like, *Pichia bovis* such as *Pichia bovis* IFO 0872 and the like, *Pichia cactophila* such as *Pichia cactophila* JCM 1830 and the like, *Pichia chambardii* IFO 1274 and the like, *Pichia fluxuum* such as *Pichia fluxuum* JCM 3646 and the like, *Pichia japonica* such as *Pichia japonica* IFO 1274 and the like, *Pichia lynferdii* such as *Pichia lynferdii* IFO 10724 and the like, *Pichia manshurica* such as *Pichia manshurica* IFO 0181, *Pichia manshurica* IFO 0864 and the like, *Pichia misumaiensis* such as *Pichia misumaiensis* IFO 10221 and the like, *Pichia naganishii* such as *Pichia naganishii* IFO 1670 and the like, *Pichia nahasei* such as *Pichia nahasei* JCM 1699 and the like, *Pichia nakazawae* such as *Pichia nakazawae* var. *akitaensis* JCM 10738, *Pichia nakazawae* var. *nakazawae* JCM 7529 and the like, *Pichia philogaea* such as *Pichia philogaea* JCM 10739 and the like, *Pichia rhodanensis* such as *Pichia rhodanensis* JCM 3649 and the like, *Pichia silvicola* such as *Pichia silvicola* JCM 3627 and the like, *Pichia subpelliculosa* such as *Pichia subpelliculosa* IFO 0808 and the like, *Pichia toletana* such as *Pichia toletana* IFO 1275 and the like, *Pichia trehalophila* such as *Pichia trehalophila* JCM 3651 and the like, *Pichia triangularis* such as *Pichia triangularis* JCM 2379 and the like, and *Pichia veronae* such as *Pichia veronae* IFO 1667 and the like.

Preferred examples of the microorganism belonging to the genus *Saccharomyces* include *Saccharomyces exiguus* such as *Saccharomyces exiguus* IFO 1170 and the like.

In addition, examples of the microorganism which has the ability to produce S-form 3-hydroxy-3-(2-thienyl)propionic acid ester derivatives by stereoselectively reducing the β-ketocarbonyl compound represented by the aforementioned general formula (3) include microorganisms belonging to the genus *Ambroziozyma*, the genus *Brettanomyces*, the genus *Brevibacterium*, the genus *Bullera*, the genus *Candida*, the genus *Citeromyces*, the genus *Corynebacterium*, the genus *Cryptococcus*, the genus *Cystofilobasidium*, the genus *Debaryomyces*, the genus *Dekkera*, the genus *Endomyces*, the genus *Exophiala*, the genus *Fellomyces*, the genus *Filobasidium*, the genus *Hanseniaspora*, the genus *Holtezmannia*, the genus *Issatchenkia*, the genus *Kloeckera*, the genus *Kluyveromyces*, the genus *Komagataella*, the genus *Lipomyces*, the genus *Lodderomyces*, the genus *Metschnikowia*, the genus *Ogataea*, the genus *Rhodotorula*, the genus *Saccharomyces*, the genus *Saccharomycopsis*, the genus *Saitoella*, the genus *Shizosaccharomyces*, the genus *Sirobasidium*, the genus *Sporidiobolus*, the genus *Sterigmatomyces*, the genus *Sterigmatosporidium*, the genus *Torulaspora*, the genus *Tremella*, the genus *Trichosporon*, the genus *Trichosporonoides*, the genus *Trigonopsis*, the genus *Waltomyces*, the genus *Wickerhamiella*, the genus *Williopsis*, the genus *Yamadazyma* and the genus *Yarrowia*.

Preferred examples of the microorganism belonging to the genus *Ambroziozyma* include *Ambroziozyma ambrosiae* such as *Ambroziozyma ambrosiae* IFO 10835 and the like, *Ambroziozyma cicatricosa* such as *Ambroziozyma cicatricosa* JCM 7598 and the like, *Ambroziozyma monospora* such as *Ambroziozyma monospora* IFO 1965, *Ambroziozyrna monospora* JCM 7599 and the like, *Ambroziozyma philentoma* such as *Ambroziozyma philentoma* JCM 7600 and the like, and *Ambroziozyma platypodis* such as *Ambroziozyma platypodis* IFO 1471 and the like.

Preferred examples of the microorganism belonging to the genus *Brettanomyces* include *Brettanomyces anomalus* such as *Brettanomyces anomalus* IFO 0627 and the like, *Brettanomyces bruxellensis* such as *Brettanomyces bruxellensis* IFO 0629, *Brettanomyces bruxellensis* IFO 0797 and the like, and *Brettanomyces naardenensis* such as *Brettanomyces naardenensis* IFO 1588 and the like.

Preferred examples of the microorganism belonging to the genus *Brevibacterium* include *Brevibacterium saccharolyticum* such as *Brevibacterium saccharolyticum* ATCC 14066 and the like.

Preferred examples of the microorganism belonging to the genus *Bullera* include *Bullera pseudoalba* such as *Bullera*

*pseudoalba* JCM 5290 and the like, and *Bullera unica* such as *Bullera unica* JCM 8932 and the like.

Preferred examples of the microorganism belonging to the genus *Candida* include *Candida lambica* such as *Candida lambica* JCM 9557 and the like, *Candida boidinii* such as *Candida boidinii* IFO 10035, *Candida boidinii* IFO 10240, *Candida boidinii* IFO 10329, *Candida boidinii* IFO 10574 and the like, *Candida cylindracea* such as *Candida cylindracea* ATCC 14830 and the like, *Candida deserticola* such as *Candida deserticola* IFO 10232 and the like, *Candida famata* such as *Candida famata* ATCC 20850, *Candida famata* var. *famata* IFO 0856 and the like, *Candida glabrata* such as *Candida glabrata* ATCC 15126, *Candida glabrata* IFO 0005, *Candida glabrata* IFO 0622 and the like, *Candida glaebosa* such as *Candida glaebosa* IFO 1353 and the like, *Candida globosa* such as *Candida globosa* IFO 0953 and the like, *Candida gropengiesseri* such as *Candida gropengiesseri* IFO 0659 and the like, *Candida intermedia* such as *Candida intermedia* IFO 0761 and the like, *Candida krusei* such as *Candida krusei* IFO 0201, *Candida krusei* IFO 1162, *Candida krusei* IFO 1664, *Candida krusei* JCM 2284, *Candida krusei* JCM 2341 and the like, *Candida magnoliae* such as *Candida magnoliae* IFO 0705 and the like, *Candida maitosa* such as *Candida maitosa* IFO 1977 and the like, *Candida melinii* such as *Candida melinii* IFO 0747, *Candida melinii* JCM 2276 and the like, *Candida molischiana* such as *Candida molischiana* IFO 10296 and the like, *Candida norvegensis* such as *Candida norvegensis* JCM 2307 and the like, *Candida parapsilosis* such as *Candida parapsilosis* IFO 0585 and the like, *Candida pini* such as *Candida pini* IFO 1327 and the like, *Candida quercuum* such as *Candida quercuum* IFO 1576 and the like, *Candida rugosa* such as *Candida rugosa* IFO 0591 and the like, *Candida sake* such as *Candida sakee* IFO 0435 and the like, *Candida solani* such as *Candida solani* IFO 0762 and the like, *Candida tropicalis* such as *Candida tropicalis* IFO 0006, *Candida tropicalis* IFO 0199, *Candida tropicalis* IFO 0618, *Candida tropicalis* IFO 1647 and the like, *Candida utilis* such as *Candida utilis* IAM 4961, *Candida utilis* IFO 0396 and the like, *Candida vartiovaarae* such as *Candida vartiovaarae* JCM 3759 and the like, and *Candida zeylanoides* such as *Candida zeylanoides* CBS 6408, *Candida zeylanoides* IFO 10325, *Candida zeylanoides* JCM 1627 and the like.

Preferred examples of the microorganism belonging to the genus *Citeromyces* include *Citeromyces matritensis* such as *Citeromyces matritensis* IFO 0954, *Citeromyces matritensis* IFO 0651 and the like.

Preferred examples of the microorganism belonging to the genus *Corynebacterium* include *Corynebacterium acetoacidophilum* such as *Corynebacterium acetoacidophilum* ATCC 13870 and the like, *Corynebacterium ammoniagenes* such as *Corynebacterium anmoniagenes* JCM 1305 and the like, *Corynebacterium flavescens* such as *Corynebacterium flavescens* JCM 1317 and the like, *Corynebacterium glutamicum* such as *Corynebacterium glutamicum* ATCC 13032, *Corynebacterium glutamicum* ATCC 13826, *Corynebacterium glutamicum* ATCC 13869 and the like, and *Corynebacterium variabile* such as *Corynebacterium variabile* JCM 2154 and the like.

Preferred examples of the microorganism belonging to the genus *Cryptococcus* include *Cryptococcus aerius* such as *Cryptococcus aerius* IFO 0377, *Cryptococcus aerius* IFO 1322 and the like, *Cryptococcus albidus* such as *Cryptococcus albidus* IFO 0612, *Cryptococcus albidus* IFO 0378, *Cryptococcus albidus* IFO 0612 and the like, *Cryptococcus cellulolyticus* such as *Cryptococcus cellulolyticus* JCM 9707 and the like, *Cryptococcus curvatus* such as *Cryptococcus curvatus* IFO 1159 and the like, *Cryptococcus heveanensis* such as *Cryptococcus heveanensis* JCM 3693 and the like, *Cryptococcus laurentii* such as *Cryptococcus laurentii* DSM 70766, *Cryptococcus laurentii* IFO 1898, *Cryptococcus laurentii* var. *laurentii* CBS 2174, *Cryptococcus laurentii* var. *laurentii* CBS 5297, *Cryptococcus laurentii* var. *laurentii* CBS 5746, *Cryptococcus laurentii* var. *laurentii* CBS 7140 and the like, *Cryptococcus luteolus* such as *Cryptococcus luteolus* IFO 0411 and the like, *Cryptococcus magnus* such as *Cryptococcus magnus* JCM 9038 and the like, *Cryptococcus terreus* such as *Cryptococcus terreus* IFO 0727, *Cryptococcus terreus* JCM 8975 and the like, and *Cryptococcus yarrowii* such as *Cryptococcus yarrowii* JCM 8232 and the like.

Preferred examples of the microorganism belonging to the genus *Cystofilobasidium* include *Cystofilobasidium bisporidii* such as *Cystofilobasidium bisporidii* JCM 9050 and the like, *Cystofilobasidium capitatum* such as *Cystofilobasidium capitatum* JCM 3793 and the like, and *Cystofilobasidium infirmominiatum* such as *Cystofilobasidium infirmominiatum* JCM 3797, *Cystofilobasidium infirmominiatum* JCM 8159 and the like.

Preferred examples of the microorganism belonging to the genus *Debaryomyces* include *Debaryomyces hansenii* such as *Debaryomyces hansenii* var. *fabryi* JCM 1441, *Debaryomyces hansenii* var. *fabryi* JCM 2104, *Debaryomyces hansenii* var. *hansenii* IFO 0032, *Debaryomyces hansenii* var. *hansenii* IFO 0034, *Debaryomyces hansenii* var. *hansenii* IFO 0060, *Debaryomyces hansenii* var. *hansenii* IFO 0855, *Debaryomyces hansenii* var. *hansenii* JCM 1521, *Debaryomyces hansenii* var. *hansenii* JCM 2192, *Debaryomyces hansenii* var. *hansenii* JCM 2194, *Debaryomyces hansenii* var. *hansenii* JCM 2196 and the like, *Debaryomyces polymorphus* such as *Deharyomyces polymorphus* JCM 3647 and the like, *Debaryomyces pseudopolymorphus* such as *Debaryomyces pseudopolymorphus* JCM 3652 and the like, *Debaryomyces robertsiae* such as *Debaryomyces robertsiae* IFO 1277 and the like, and *Debaryomyces vanrijiae* such as *Debaryomyces vanrijiae* var. *vanrijiae* JCM 3657, *Debaryomyces vanrijiae* var. *yarrowii* JCM 6190 and the like.

Preferred examples of the microorganism belonging to the genus *Dekkera* include *Dekkera bruxellensis* such as *Dekkera bruxellensis* CBS 2796 and the like.

Preferred examples of the microorganism belonging to the genus *Endomyces* include *Endomyces decipiens* such as *Endomyces decipiens* IFO 0102 and the like.

Preferred examples of the microorganism belonging to the genus *Exophiala* include *Exophiala dermatitidis* such as *Exophiala dermatitidis* IFO 6421, *Exophiala dermatitidis* IFO 8193 and the like.

Preferred examples of the microorganism belonging to the genus *Fellomyces* include *Fellomyces fuzhouensis* such as *Fellomyces fuzhouensis* IFO 10374 and the like.

Preferred examples of the microorganism belonging to the genus *Filobasidium* include *Filobasidium capsuligenum* such as *Filobasidium capsuligenum* IFO 1119, *Filobasidium capsuligenum* IFO 1185 and the like, *Filobasidium elegans* such as *Filobasidium elegans* IFO 10881 and the like, *Filobasidium floriforme* such as *Filobasidium floriforme* IFO 10886, *Filobasidium floriforme* IFO 1603 and the like, *Filobasidium globisporum* such as *Filobasidium globisporum* IFO 10887 and the like, and *Filobasidium uniguttulatum* such as *Filobasidium uniguttulatum* IFO 0699 and the like.

Preferred examples of the microorganism belonging to the genus *Hanseniaspora* include *Hanseniaspora guilliermondii* such as *Hanseniaspora guilliermondii* IFO 1411 and the like, and *Hanseniaspora uvarum* such as *Hanseniaspora uvarum* IFO 1755 and the like.

Preferred examples of the microorganism belonging to the genus *Holtermannia* include *Holtermannia cornifomis* such as *Holtermannia cornifoamis* JCM 1743 and the like.

Preferred examples of the microorganism belonging to the genus *Issatchenkia* include *Issatchenkia orientalis* such as *Issatchenkia orientalis* IFO 1279 and the like, *Issatchenkia scutulata* such as *Issatchenkia scutulata* var. *exigua* JCM 1829, *Issatchenkia scutulata* var. *scutulata* JCM 1828 and the like, and *Issatchenkia terricola* such as *Issatchenkia terricola* IFO 0933, *Issatchenkia terricola* IFO 1907 and the like.

Preferred examples of the microorganism belonging to the genus *Kloeckera* include *Kloeckera apiculata* such as *Kloeckera apiculata* IFO 0865 and the like and *Kloeckera japonica* such as *Kloeckera japonica* IFO 0151 and the like.

Preferred examples of the microorganism belonging to the genus *Kluyveromyces* include *Kluyveromyces lactis* such as *Kluyveromyces lactis* var. *lactis* IFO 1267 and the like, *Kluyveromyces marxianus* such as *Kluyveromyces marxianus* CBS 834 and the like, and *Kluyveromyces thermotolerans* such as *Kluyveromyces thermotolerans* IFO 1674, *Kluyveromyces thermotolerans* IFO 1779, *Kluyveromyces thermotolerans* IFO 0662, *Kluyveromyces thermotolerans* IFO 1050, *Kluyveromyces thermotolerans* IFO 1780, *Kluyveromyces thermotolerans* IFO 1985 and the like.

Preferred examples of the microorganism belonging to the genus *Komagataella* include *Komagataella pastoris* such as *Komagataella pastoris* ATCC 28485, *Komagataella pastoris* IFO 0948, *Komagataella pastoris* IFO 1013 and the like.

Preferred examples of the microorganism belonging to the genus *Lipomyces* include *Lipomyces tetrasporus* such as *Lipomyces tetrasporus* IFO 10391 and the like.

Preferred examples of the microorganism belonging to the genus *Lodderomyces* include *Lodderomyces elongisporus* such as *Lodderomyces elongisporus* IFO 1676 and the like.

Preferred examples of the microorganism belonging to the genus *Metschnikowia* include *Metschnikowia agaves* such as *Metschnikowia agaves* IFO 10860 and the like, *Metschnikowia australis* such as *Metschnikowia australis* IFO 10783 and the like, *Metschnikowia bicuspidata* such as *Metschnikowia bicuspidate* var. *bicuspidata* IFO 1408, *Metschnikowia bicuspidate* var. *chathamia* IFO 10785 and the like, *Metschnikowia gruessii* such as *Metschnikowia gruessii* IFO 10788 and the like, *Metschnikowia hawaiiensis* such as *Metschnikowia hawaiiensis* IFO 10791 and the like, *Metschnikowia lunata* such as *Metschnikowia lunata* IFO 1605 and the like, *Metschnikowia reukaufii* such as *Metschnikowia reukaufii* IFO 10798, *Metschnikowia reukaufii* IFO 1679, *Metschnikowia reukaufii* JCM 2279 and the like, *Metschnikowia zobellii* such as *Metschnikowia zobellii* IFO 10800, *Metschnikowia zobellii* IFO 1680 and the like, and *Metschnikowia* sp. such as *Metschnikowia* sp. IFO 1406 and the like.

Preferred examples of the microorganism belonging to the genus *Ogataea* include *Ogataea minuta* such as *Ogataea minuta* var. *minuta* IFO 0975, *Ogataea minuta* var. *nonfermentans* IFO 1473 and the like, and *Ogataea polymorpha* such as *Ogataea polymorpha* IFO 1475 and the like.

Preferred examples of the microorganism belonging to the genus *Pichia* include *Pichia amylophila* such as *Pichia amylophila* JCM 1702 and the like, *Pichia anomala* such as *Pichia anomala* IFO 0118 and the like, *Pichia augusta* such as *Pichia augusta* ATCC 26012 and the like, *Pichia barkeri* such as *Pichia barkeri* IFO 10714 and the like, *Pichia besseyi* such as *Pichia besseyi* JCM 1706 and the like, *Pichia bimundalis* such as *Pichia bimundalis* JCM 3591 and the like, *Pichia bispora* such as *Pichia bispora* JCM 3590 and the like, *Pichia canadensis* such as *Pichia canadensis* JCM 3597 and the like, *Pichia castillae* such as *Pichia castillae* JCM 10733 and the like, *Pichia delftensis* such as *Pichia delftensis* IFO 10715 and the like, *Pichia deserticola* such as *Pichia deserticola* IFO 10716 and the like, *Pichia dryadoides* such as *Pichia dryadoides* IFO 1820 and the like, *Pichia euphorbiiphila* such as *Pichia euphorbiiphila* IFO 10717 and the like, *Pichia fabianii* such as *Pichia fabianii* JCM 3601 and the like, *Pichia fermentans* such as *Pichia fermentans* JCM 2189 and the like, *Pichia hanpshirensis* such as *Pichia hanpshirensis* IFO 10719 and the like, *Pichia heedii* such as *Pichia heedii* JCM 1833 and the like, *Pichia heimii* such as *Pichia heimii* IFO 1686 and the like, *Pichia inositovora* such as *Pichia inositovora* JCM 10736 and the like, *Pichia jadinii* such as *Pichia jadinii* JCM 3617 and the like, *Pichia kluyveri* such as *Pichia kluyveri* var. *cephalocereana* IFO 10722, *Pichia kluyveri* var. *eremophila* IFO 10723, *Pichia kluyveri* var. *kluyveri* IFO 1165 and the like, *Pichia media* such as *Pichia media* JCM 10737 and the like, *Pichia methanolica* such as *Pichia methanolica* ATCC 58403 and the like, *Pichia methylivora* such as *Pichia methylivora* IFO 10705 and the like, *Pichia mexicana* such as *Pichia mexicana* JCM 1835 and the like, *Pichia meyerae* such as *Pichia meyerae* IFO 10727 and the like, *Pichia mississippiensis* such as *Pichia mississippiensis* JCM 1703 and the like, *Pichia norvegensis* such as *Pichia norvegensis* IFO 1694 and the like, *Pichia onychis* such as *Pichia onychis* IFO 1682 and the like, *Pichia petersonii* such as *Pichia petersonii* IFO 1372 and the like, *Pichia pijperi* such as *Pichia pijperi* IFO 1290 and the like, *Pichia populi* such as *Pichia populi* IFO 10729 and the like, *Pichia pseudocactophila* such as *Pichia pseudocactophila* IFO 10730 and the like, *Pichia quercuum* such as *Pichia quercuum* JCM 3659 and the like, *Pichia rabaulensis* such as *Pichia rabaulensis* IFO 1643 and the like, *Pichia salicaria* such as *Pichia salicaria* JCM 3653 and the like, *Pichia scolyti* such as *Pichia scolyti* JCM 3654 and the like, *Pichia segobiensis* such as *Pichia segobiensis* JCM 10740 and the like, *Pichia spartinae* such as *Pichia spartinae* JCM 10741 and the like, *Pichia strasburgensis* such as *Pichia strasburgensis* JCM 3660 and the like, *Pichia sydowiorum* such as *Pichia sydowiorum* JCM 9455 and the like, *Pichia tannicola* such as *Pichia tannicola* JCM 8120 and the like, and *Pichia wickerhamii* such as *Pichia wickerhamii* JCM 3654 and the like.

Preferred examples of the microorganism belonging to the genus *Rhodotorula* include *Rhodotorula aurantiaca* such as *Rhodotorula aurantiaca* IFO 0754 and the like, *Rhodotorula fragaria* such as *Rhodotorula fragaria* JCM 3930 and the like, *Rhodotorula glutinis* such as *Rhodotorula glutinis* var. *dairenensis* IFO 0415 and the like, *Rhodotorula graminis* such as *Rhodotorula graminis* JCM 3775 and the like, *Rhodotorula bordea* such as *Rhodotorula bordea* JCM 3932 and the like, *Rhodotorula hylophila* such as *Rhodotorula hylophila* JCM 1805 and the like, *Rhodotorula ingeniosa* such as *Rhodotorula ingeniosa* JCM 9031 and the like, *Rhodotorula javanica* such as *Rhodotorula javanica* JCM 9032 and the like, *Rhodotorula minuta* such as *Rhodotorula minuta* IFO 0715, *Rhodotorula minuta* IFO 0920, *Rhodotorula minuta* JCM 3776, *Rhodotorula minuta* IFO 0387 and the like, *Rhodotorula mucilaginosa* such as *Rhodotorula mucilaginosa* IFO 0870 and the like, *Rhodotorula muscorum* such as *Rhodotorula muscorum* JCM 1697 and the like, and *Rhodotorula pustula* such as *Rhodotorula pustula* JCM 3934 and the like.

Preferred examples of the microorganism belonging to the genus *Saccharomyces* include *Saccharomyces cerevisiae* such as *Saccharomyces cerevisiae* IFO 0305, *Saccharomyces cerevisiae* IFO 0565, *Saccharomyces cerevisiae* JCM 1818 and the like, and *Saccharomyces ludwigii* such as *Saccharomyces ludwigii* IFO 0798 and the like.

Preferred examples of the microorganism belonging to the genus *Saccharomycopsis* include *Saccharomycopsis fibuligera* such as *Saccharomycopsis fibuligera* IFO 0105, *Saccharomycopsis fibuligera* IFO 1744, *Saccharomycopsis fibuligera* IFO 0105 and the like, *Saccharomycopsis malanga* such as *Saccharomycopsis malanga* IFO 1710 and the like, *Saccharomycopsis schoenii* such as *Saccharomycopsis schoenii* IFO 1579 and the like, and *Saccharomycopsis synnaedendra* such as *Saccharomycopsis synnaedendra* IFO 1604 and the like.

Preferred examples of the microorganism belonging to the genus *Saitoella* include *Saitoella complicata* such as *Saitoella complicata* IAM 12963 and the like.

Preferred examples of the microorganism belonging to the genus *Schizoblastosporion* include *Schizoblastosporion chiloense* such as *Schizoblastosporion chiloense* IFO 10841 and the like.

Preferred examples of the microorganism belonging to the genus *Shizosaccharomyces* include *Shizosaccharomyces japonicus* such as *Shizosaccharomyces japonicus* JCM 8263 and the like, *Shizosaccharomyces octosporus* such as *Shizosaccharomyces octosporus* IFO 10373 and the like, and *Shizosaccharomyces pombe* such as *Shizosaccharomyces pombe* IFO 1628, *Shizosaccharomyces pombe* IFO 0344, and the like.

Preferred examples of the microorganism belonging to the genus *Sirobasidium* include *Sirobasidium magnum* such as *Sirobasidium magnum* JCM 6876 and the like.

Preferred examples of the microorganism belonging to the genus *Sporidiobolus* include *Sporidiobolus johnsonii* such as *Sporidiobolus johnsonii* IFO 6903 and the like.

Preferred examples of the microorganism belonging to the genus *Sterigmatomyces* include *Sterigmatomyces halophilus* such as *Sterigmatomyces halophilus* IFO 1488 and the like. Preferred examples of the microorganism belonging to the genus *Sterigmatosporidium* include *Sterigmatosporidium polymorphum* such as *Sterigmatosporidium polymorphum* JCM 6902 and the like.

Preferred examples of the microorganism belonging to the genus *Torulaspora* include *Torulaspora delbrueckii* such as *Torulaspora delbrueckii* CBS 1146 and the like.

Preferred examples of the microorganism belonging to the genus *Tremella* include *Tremella aurantia* such as *Tremella aurantia* JCM 1327 and the like, *Tremella encephala* such as *Tremella encephala* JCM 11329 and the like, and *Tremella foliacea* such as *Tremella foliacea* JCM 11330 and the like.

Preferred examples of the microorganism belonging to the genus *Trichosporon* include *Trichosporon domesticum* such as *Trichosporon domesticum* JCM 9580 and the like, *Trichosporon laibachii* such as *Trichosporon laibachii* JCM 9934 and the like, *Trichosporon montevideense* such as *Trichosporon montevideense* JCM 9937 and the like, *Trichosporon mucoides* such as *Trichosporon mucoides* JCM 9939 and the like, and *Trichosporon* sp. such as *Trichosporon* sp. IFO 116 and the like.

Preferred examples of the microorganism belonging to the genus *Trichosporonoides* include *Trichosporonoides megachiliensis* such as *Trichosporonoides megachiliensis* CBS 567.85 and the like, and *Trichosporonoides oedocephalis* such as *Trichosporonoides oedocephalis* CBS 568.85 and the like.

Preferred examples of the microorganism belonging to the genus *Trigonopsis* include *Trigonopsis variabilis* such as *Trigonopsis variabilis* CBS 4095, *Trigonopsis variabilis* CBS 4069, *Trigonopsis variabilis* IFO 0671 and the like.

Preferred examples of the microorganism belonging to the genus *Waltomyces* include *Waltomyces lipofer* such as *Waltomyces lipofer* IFO 1288 and the like.

Preferred examples of the microorganism belonging to the genus *Wickerhamiella* include *Wickerhamiella domercqiae* such as *Wickerhamiella domercqiae* IFO 1857 and the like.

Preferred examples of the microorganism belonging to the genus *Williopsis* include *Williopsis californica* such as *Williopsis californica* JCM 3600, *Williopsis californica* JCM 3605 and the like, *Williopsis mucosa* such as *Williopsis mucosa* JCM 6809 and the like, and *Williopsis saturnus* such as *Williopsis saturnus* var. *mrakii* JCM 3614, *Williopsis saturnus* var. *sargentensis* IFO 1826, *Williopsis saturnus* var. *saturnus* IFO 10697, *Williopsis saturnus* var. *saturnus* JCM 3594, *Williopsis saturnus* var. *saturnus* JCM 3595, *Williopsis saturnus* var. *saturnus* JCM 3596, *Williopsis saturnus* var. *saturnus* JCM 3623, *Williopsis saturnus* var. *saturnus* JCM 3624, *Williopsis saturnus* var. *saturnus* JCM 9398, *Williopsis saturnus* var. *suaveolens* IFO 10698, *Williopsis saturnus* var. *subsufficiens* JCM 3625, *Williopsis saturnus* var. *subsufficiens* JCM 3626 and the like.

Preferred examples of the microorganism belonging to the genus *Yamadazyma* include *Yamadazyma farinosa* such as *Yamadazyma farinosa* IFO 0193, *Yamadazyma farinosa* IFO 10061, *Yamadazyma haplophila* IFO 0947 and the like.

Preferred examples of the microorganism belonging to the genus *Yarrowia* include *Yarrowia lipolytica* such as *Yarrowia lipolytica* ATCC 8661, *Yarrowia lipolytica* IFO 1209, *Yarrowia lipolytica* IFO 1548 and the like.

In this connection, among the aforementioned microorganisms, the microorganisms having IFO numbers are described in the internet catalogue (http://www.ifo.or.jp) of Institute for Fermentation, Osaka (IFO), and can be obtained from said IFO.

The microorganisms having CBS numbers are described in the internet catalogue (http://www.cbs.knaw.nl) of The Centraalbureau voor Schimmelcultures (CBS), and can be obtained from said CBS.

The microorganisms having ATCC numbers are described in the internet catalogue (http://www.atcc.org) of American Type Culture Collection (ATCC), and can be obtained from said ATCC.

The microorganisms having IAM numbers are described in the internet catalogue (http://www.iam.u-tokyo.ac.jo/misyst/ColleBOX/IAMcollection.html) of IAM Culture Collection (IAM), and can be obtained from said IAM.

The microorganisms having JCM numbers are described in the internet catalogue (http://www.jcm.riken.go.jp) of Japanese Collection of Microorganisms (JCM), and can be obtained from said JCM.

In addition, each of the aforementioned microorganisms may be any strain such as a mutant strain obtained by the UV irradiation, nitrosoguanidine treatment or the like general mutation treatment, or a recombinant strain obtained by cell fusion or induced by genetic recombination technique or the like genetic method.

Also, as expression strains of a recombinant strain, *Escherichia coli* or the like bacterium, yeast or the like may be used instead of the original strain, and these recombinant strains are also included in the general idea as the aforementioned microorganisms.

According to the production method of the present invention, one or two or more species of the aforementioned microorganisms are used as the cells, treated product of the cells and/or culture medium.

Illustratively, cells obtained by culturing the aforementioned microorganism or a culture medium thereof can be used as such, or a treated product of cells such as a product obtained by treating the cultured cells by a conventionally known method, such as acetone treatment, air-drying or freeze-drying, or a product obtained by physically, chemically or enzymatically disrupting the calls, can also be used.

Also, it is possible to use an enzyme fraction having the ability to react upon the 3-oxo-3-(2-thienyl)propionic acid ester derivative of formula (I) and thereby convert it into the optically active 3-hydroxy-3-(2-thienyl)propionic acid ester derivative of formula (ii) or formula (III), by preparing the fraction from these cells or a treated product of the cells as a crude substance or purified substance. It is possible also to use those in which the cells, a treated product of the cells, an enzyme fraction and the like obtained in this manner are immobilized on polyacrylamide, carrageenan gel and the lie carriers using general immobilization techniques. Accordingly, the term "a cell and/or a treated product of said cell" as used in this specification is used as a general idea which includes all of the aforementioned cells, treated products of the cells, enzyme fractions and immobilized products thereof.

In addition, the aforementioned microorganisms are generally used by culturing them, and this culturing can be carried out in the usual way. The medium to be used for the culturing of such microorganisms contains carbon sources, nitrogen sources, inorganic ions and the like which can be assimilated by these microorganisms. As the carbon sources, glucose, fructose, sucrose and the like carbohydrates, glycerol, mannitol, xylitol, sorbitol and the like poyalcohols, organic acids and the others are optionally used. As the nitrogen sources, NZ amine, tryptose, yeast extract, polypeptone, meat extract, soybean extract and the like organic nitrogen sources, or ammonium sulfate, ammonium nitrate and the like inorganic nitrogen sources, and other substances are optionally used. As the inorganic ions, phosphate ion, magnesium ion, iron ion, manganese ion, molybdenum ion and the like are optionally used as occasion demands. The culturing is carried out under an aerobic condition for a period of from 1 to 100 hours, while controlling the medium pH at about 3 to 10, preferably pH 6 to 8, and a temperature at from 4 to 50° C., preferably from 25 to 40° C.

(Asymmetric Reduction)

In the production method of the present invention, a 3-oxo-3-(2-thienyl)propionic acid ester derivative represented by the aforementioned general formula (3) is used as the material, and an optically active 3-hydroxy-3-(2-thienyl)propionic acid ester derivative is produced by allowing cells, a treated product of said cells and/or a culture medium of the aforementioned microorganism to react upon this material.

Examples of the reaction method include a) a method in which a 3-oxo-3-(2-thienyl)propionic acid ester derivative represented by the aforementioned general formula (3) is allowed to contact with cells, a treated product of said cells and/or a culture medium of the aforementioned microorganism in an aqueous medium and b) a method in which the culturing and reaction are simultaneously carried out using a medium containing a 3-oxo-3-(2-thienyl)propionic acid ester derivative represented by the aforementioned general formula (3), and these can be optionally used, but the aforementioned method a) is industrially desirable because of the absence of energy loss used for the microbial growth.

It is desirable that the concentration of a 3-oxo-3-(2-thienyl)propionic acid ester derivative represented by the aforementioned general formula (3) in the reaction system is within the range of from 0.0001 to 50% (w/v), preferably from 0.01 to 5% (w/v), and the 3-oxo-3-(2-thienyl)propionic acid ester derivative may be successively added during the reaction as occasion demands.

As the aforementioned aqueous medium, an aqueous solution containing potassium phosphate, Tris-HCl or the like and having buffer action is generally used, but the buffer components can be omitted in case that change in the pH value is controlled with hydrochloric acid, sodium hydroxide and the like acid and alkali by monitoring the pH during the reaction.

Also, for the purpose of increasing solubility of the substrate, methanol, ethanol, isopropyl alcohol, acetone, dioxane, acetonitrile, tetrahydrofuran, dimethylformamide, dimethyl sulfoxide or the like hydrophilic solvent may be added, or Tween 80, a sugar ester or the like surface active agent may be added for the same purpose.

In addition, in order to control reaction inhibition by the substrate and product, ethyl acetate, butyl acetate, hexane, isopropyl ether, carbon tetrachloride, 1-octanol or the like hydrophobic solvent can also be added in an amount of approximately from 0.1 to 10 volumes of the reaction solution.

It is desirable that glucose, ethanol, isopropyl alcohol, formic acid or the like is contained in the reaction solution as the energy source of the reduction reaction in an amount of from 1 to 20 moles of based on the substrate.

Also, it is effective to add oxidized type or reduced type nicotinamide adenine dinucleotide (NAD) or nicotinamide adenine dinucleotide phosphate (NADP) to be used as the coenzyme in the reduction reaction in an amount of from 0.001 to 0.1% (w/v).

In addition, supplement with glucose dehydrogenase, alcohol dehydrogenase, formate dehydrogenase or the like is also effective for accelerating regeneration of the coenzyme into reduced type.

Though the reaction conditions vary depending on the kind of microorganism, the reaction is carried out at a temperature within the range of generally from 4 to 70° C., preferably from 20 to 50° C., more preferably from 28 to 42° C., and at a pH within the range of generally from 3 to 10, preferably from 5 to 9, more preferably from 6 to 8.

The reaction system may be either a batch system or a continuous system, but in the case of a continuous system, it is carried out by optionally adding a 3-oxo-3-(2-thienyl)propionic acid ester derivative of the formula (I), a microbial culture medium, cells and/or a treated product of said cells as occasion demands, and the cells separated from the product of interest may be used by recycling them.

Regarding the method for collecting the optically active 3-hydroxy-3-(2-thienyl)propionic acid ester derivative obtained by the aforementioned reaction, it can be separated by removing microorganism and the like solid matter using a centrifuge, a filter press, an ultrafiltration device or the like general separation apparatus, and then subjecting the reaction solution to organic solvent extraction, crystallization, column chromatography, concentration, distillation and the like separation purification means, and the separation purification means can be employed alone or in combination of two or more means.

Examples of the organic solvent to be used in the extraction include butanol and the like alcohols, hexane, cyclohexane, toluene and the like hydrocarbons, chloroform, methylene chloride and the like halogenated hydrocarbons, ethyl acetate, normal butyl acetate and the like esters, ketones, ethers, mixed solvents thereof and the like.

B-3) Optically Active 3-hydroxy-3-(2-thienyl)propionic acid ester compound

The optically active 3-hydroxy-3-(2-thienyl)propionic acid ester compound represented by the general formula (3') obtained in the aforementioned B-1) or B-2) is a novel compound. Illustrative examples of the aforementioned optically active 3-hydroxy-3-(2-thienyl)propionic acid ester compound include (S)-3-hydroxy-3-(2-thienyl)propionic acid methyl ester, (S)-3-hydroxy-3-(2-thienyl)propionic acid ethyl ester, (S)-3-hydroxy-3-(2-thienyl)propionic acid propyl ester, (S)-3-hydroxy-3-(2-thienyl)propionic acid isopropyl ester, (S)-3-hydroxy-3-(2-thienyl)propionic acid cyclopropyl ester, (S)-3-hydroxy-3-(2-thienyl)propionic acid butyl ester, (S)-3-hydroxy-3-(2-thienyl)propionic acid isobutyl ester, (S)-3-hydroxy-3-(2-thienyl)propionic acid tert-butyl ester, (R)-3-hydroxy-3-(2-thienyl)propionic acid methyl ester, (R)-3-hydroxy-3-(2-thienyl)propionic acid ethyl ester, (R)-3-hydroxy-3-(2-thienyl)propionic acid propyl ester, (R)-3-hydroxy-3-(2-thienyl)propionic acid isopropyl ester, (R)-3-hydroxy-3-(2-thienyl)propionic acid cyclopropyl ester, (R)-3-hydroxy-3-(2-thienyl)propionic acid butyl ester, (R)-3-hydroxy-3-(2-thienyl)propionic acid isobutyl ester, (R)-3-hydroxy-3-(2-thienyl)propionic acid tert-butyl ester and the like.

B-4) Amidation

The optically active 3-hydroxy-3-(2-thienyl)propionic acid ester compound represented by the general formula (3') obtained in the aforementioned B-1) or B-2) can be converted into a compound represented by the aforementioned general formula (1) by allowing it to react with amines represented by $R^1R^{1'}NH$ ($R^1$ and $R^{1'}$ are as defined in the foregoing) to effect its amidation, by the same method described in a part of the aforementioned item B) regarding the amidation reaction of a compound represented by the general formula (3).

C) Reduction Reaction of Amido Group

As the method for reducing amido group of the aforementioned optically active 3-hydroxy-3-(2-thienyl)propionamides, a generally known amido group reducing method can be exemplified; illustratively, the reduction reaction can be carried out using a borane reducing agent or an aluminum reducing agent.

Illustrative examples of the aforementioned borane reducing agent include diborane ($B_2H_6$); or borane complexes such as tetrahydrofuran complex, diethyl ether complex, dimethylamine complex, pyridine complex, dimethyl sulfide complex, trimethylamine complex and the like of borane ($BH_3$). In addition, a method in which sodium borohydride is allowed to react with dimethyl sulfate, iodine or the like, and borane prepared in this manner in the system is used in the reaction, can also be exemplified. Among them, a dimethyl sulfide complex or tetrahydrofuran complex of borane is desirable, and the tetrahydrofuran complex is particularly desirable.

Illustrative examples of the aluminum reducing agent include aluminum hydride, sodium aluminum hydride, lithium aluminum hydride and sodium bis(2-methoxyethoxy)aluminum hydride. Among them, lithium aluminum hydride or sodium bis(2-methoxyethoxy)aluminum hydride is preferred, and sodium bis(2-methoxyethoxy)aluminum hydride (Red-Al (registered trademark) is particularly preferred because it can be industrially obtained.

Regarding the amount of the reducing agent to be used, since the number of moles of necessary hydride varies depending on the kind of amido group, it may be used in an amount of necessary equivalents or more in response to the substrate, but it is considered in general that such an agent may be used in an amount of 7 equivalents or more as hydride in the case of the amido group of a primary amine, 6 equivalents or more as hydride in the case of the amido group of a secondary amine, or 5 equivalents or more as hydride in the case of the amido group of a tertiary amine.

However, since too large amount of the reducing agent to be used is not desirable due to generation of side reactions such as hydrogenolysis of the substrate, it is used within the range of generally 30 equivalents or less, preferably 15 equivalents or less, particularly preferably 13.5 equivalents or less, as the amount of hydride based on the substrate.

As the method for contacting the substrate with a reducing agent, a method in which a reducing agent solution is added to a substrate solution, a method in which a substrate solution is added to a reducing agent solution, and the like can be exemplified, and these may be carried out by cooling the solution as occasion demands.

The solvent to be used is not particularly limited with the proviso that it does not inactivate the reducing agent, and its illustrative examples include diethyl ether, tetrahydrofuran and the like ether solvents; toluene, xylene and the like aromatic solvents; and methylene chloride, chloroform and the like halogen solvents. Among them, an ether solvent is desirable, particularly desirably tetrahydrofuran, in case that a borane reducing agent is used, and an aromatic solvent is desirable, particularly desirably toluene, in case that an aluminum reducing agent is used.

Regarding the reaction temperature, it is generally within the range of from room temperature or more to boiling point of the solvent used in case that a borane reducing agent is used, because of a tendency to cause a prolonged reaction time at a low temperature, and is within the range of generally from 0 to 100° C., preferably from 20 to 60° C., in case that an aluminum reducing agent is used. After carrying out the reaction for a predetermined period of time, the reaction is terminated by adding water (generally 0.5 volume or more and 10 volumes or less, preferably 1 volume or more and 5 volumes or less, based on the substrate) to the reaction solution while cooling using ice or the like as occasion demands. In that case, it is desirable to carry out this step by controlling pH of the treating solution within the range of 4 or more, preferably 4.5 or more, particularly preferably 4.6 or more.

In case that a borane reducing agent is used, it is desirable to carry out an acid treatment generally at a pH of less than 7, more preferably at a pH of 6 or less, more preferably at a pH of 5.5 or less, particularly preferably at a pH of 5 or less, in view of the removing efficiency of the inactivated reducing agent, and it is desirable to carry out the treatment under a basic condition when an aluminum reducing agent is used.

Regarding the acid to be used in the aforementioned acid treatment, it is not particularly limited with the proviso that pH of the reaction solution can be controlled within an appropriate range, and its illustrative examples include dilute hydrochloric acid, dilute sulfuric acid and the like mineral acids; or organic acids such as formic acid, acetic acid and the like carboxylic acids and methane sulfonate, p-toluenesulfonic acid and the like sulfonic acids, of which dilute hydrochloric acid or $C_1$ to $C_4$ carboxylic acids are desirable, and acetic acid is particularly desirable.

Regarding the base to be used in the aforementioned base treatment, an inorganic base which can be easily separated at the time of the purification after completion of the reaction is generally used. The aforementioned inorganic base is not particularly limited with the proviso that it dissolves in water, and its illustrative examples include ammonia; lithium hydroxide, sodium hydroxide, potassium hydroxide and the like alkali metal hydroxides; calcium hydroxide, barium hydroxide and the like alkaline earth metal hydroxides; sodium bicarbonate, potassium bicarbonate and the like alkali metal bicarbonates; calcium bicarbonate, barium bicarbonate and the like alkaline earth metal bicarbonates; and sodium carbonate, potassium carbonate and the like alkali metal carbonates, calcium carbonate, barium carbonate and the like alkaline earth metal carbonates. Its amount to be used may be an amount sufficient for inactivating the aluminum reducing agent. Also, the inorganic base may be used directly as a solid or gas or used in the state of an aqueous solution.

After the aforementioned treatment, the amines of interest- can be extracted with an organic solvent and then isolated by the combination of concentration, chromatographic purification, crystallization and the like general purification methods, but it is desirable to carry out respective after treatments shown in the following, from the optical purity maintenance, net yield improvement and the like points of view.

C-1) After Treatment of Reduction Reaction Using Borane Reducing Agent

When a borane reducing agent is used, it is desirable to hydrolyze the obtained boron-containing compound after completion of the reduction reaction in the coexistence of ketones and under an acidic or basic condition.

In hydrolyzing the boron-containing compound, the reaction solution after completion of the aforementioned reduction reaction may be used as such, or isolation of 3-amino-1-(2-thienyl)-1-propanols as the target product from the aforementioned reaction solution is carried out by a general isolation operation, and then the remaining organic layer containing the boron-containing compound may be used.

The hydrolysis is carried out by adding ketones and water, and further a base or acid, to the aforementioned organic layer containing the boron-containing compound, and heating the mixture. In this connection, when the reaction substrate is an optically active compound, it is desirable to carry out the hydrolysis under a basic condition for the purpose of preventing racemization of asymmetric carbon.

Though the ketone to be used is not particularly limited, ketones having a boiling point of 120° C. or less are desirable because of the easy removing operation after hydrolysis, of which 2-pentanone, 3-pentanone, methyl ethyl ketone or acetone is more desirable, and particularly desirable is methyl ethyl ketone or acetone. The ketone is used in an amount of generally from 0.1 to 100 volumes, preferably from 1 to 10 volumes, based on 3-hydroxy-3-(2-thienyl)propionamides.

Regarding the amount of water to be used in the reaction, an amount sufficient for dissolving a base or acid and hydrolyzing the boron-containing compound may be enough, but is used in an amount of generally from 1 to 100 volumes, preferably from 5 to 30 volumes, based on the formed 3-amino-1-(2-thienyl)-1-propanols.

Regarding the base, an inorganic base which can be easily separated at the time of the purification after completion of the reaction is generally used. The aforementioned inorganic base is not particularly limited with the proviso that it dissolves in water, and its illustrative examples include lithium hydroxide, sodium hydroxide, potassium hydroxide and the like alkali metal hydroxides; calcium hydroxide, barium hydroxide and the like alkaline earth metal hydroxides; sodium bicarbonate, potassium bicarbonate and the like alkali metal bicarbonates; calcium bicarbonate, barium bicarbonate and the like alkaline earth metal bicarbonates; sodium carbonate, potassium carbonate and the like alkali metal carbonates, and calcium carbonate, barium carbonate and the like alkaline earth metal carbonates. Regarding its amount to be used, an amount sufficient for hydrolyzing the boron-containing compound may be enough, but it is desirable in general to use it in an amount of 3 moles or more based on the boron reducing agent.

Regarding the acid to be used, it is not particularly limited with the proviso that pH can be appropriately controlled, and its illustrative examples include hydrochloric acid, sulfuric acid and the like mineral acids; methane sulfonate, p-toluenesulfonic acid and the like sulfonic acids; and formic acid, acetic acid, butyric acid, benzoic acid and the like carboxylic acids. It is preferably hydrochloric acid or a carboxylic acid having from 2 to 4 carbon atoms, and particularly preferably acetic acid which can be obtained at a low cost. In addition, in the case of hydrolysis under an acidic condition, it is desirable that pH in the reaction system at the time of the treatment is 3 or more. Particularly, when the reaction substrate is an optically active compound, it is desirable to carry out the aforementioned acid treatment by controlling it within the range of pH 4 or more, preferably pH 4.5 or more, particularly preferably pH 4.6 or more, for the purpose of preventing racemization of asymmetric carbon.

The reaction temperature at the time of hydrolysis is generally from 0° C. to 80° C., preferably from 20° C. to 60° C., the reaction time is generally from 30 minutes to 12 hours, and the reaction pressure is generally ordinary pressure but it may be under a pressure or under a reduced pressure as occasion demands.

After the aforementioned hydrolysis, the thus formed 3-amino-1-(2-thienyl)-1-propanols can be isolated by carrying out extraction and concentration. In this case, it is possible to obtain high purity 3-amino-1-(2-thienyl)-1-propanols as occasion demands by further purifying them using distillation, recrystallization, reprecipitation, column chromatography and the like usual purification techniques.

C-2) After Treatment of Reduction Reaction Using Aluminum Reducing Agent

It is desirable to allow the 3-amino-1-(2-thienyl)-1-propanols to contact with a water-soluble chelating agent after completion of the reduction reaction using aluminum reducing agent.

In allowing the 3-amino-1-(2-thienyl)-1-propanols to contact with a water-soluble chelating agent, it may be effective to add an organic solvent as occasion demands to the reaction solution after inactivation of the aluminum reducing agent and to use the resulting organic layer fraction as such, or it may be effective to use a solution in which crude 3-amino-1-(2-thienyl)-1-propanols extracted and concentrated from the reaction solution after inactivation of the aluminum reducing agent are re-dissolved in an organic solvent, or in which the aforementioned crude 3-amino-1-(2-thienyl)-1-propanols are isolated via crystallization, reprecipitation, column chromatography and the like purification techniques and then again dissolved in an organic solvent.

The aforementioned organic solvent is not particularly limited, with the proviso that it dissolves 3-amino-1-(2-thienyl)-1-propanols and separates from water, and its illustrative examples include diethyl ether, n-propyl ether, isopropyl ether, tert-butyl methyl ether and the like ethers; hexane, heptane, octane and the like aliphatic hydrocarbons; benzene, toluene, xylene and the like aromatic hydrocarbons; ethyl acetate, propyl acetate, butyl acetate and the like esters; and methylene chloride, chloroform and the like halogenated hydrocarbons, of which particularly desirable is ethyl acetate or toluene which has high solubility of hydroxyalkylamines and can be obtained at a low cost. The aforementioned solvents may be used alone or as a mixture of two or more.

Regarding the amount of the solvent to be used, an amount in which the formed hydroxyalkylamine can be sufficiently dissolved may be enough. In general, it is used in an amount of from 1 to 100 volumes, preferably from 5 to 30 volumes, based on the hydroxyalkylamine.

(Chelating Agent)

The water-soluble chelating agent is not particularly limited, with the proviso that it forms a water-soluble complex of aluminum, and its illustrative examples include oxalic acid, tartaric acid, malic acid, lactic acid, citric acid, mandelic acid and the like hydroxycarboxylic acids; diammonium tartarate, dipotassium tartarate, disodium tartarate, potassium sodium tartarate, potassium tartarate, sodium tartarate and the like sodium, potassium and ammonium salts of the aforementioned hydroxycarboxylic acids; nitrilotriacetic acid (NTA), ethylenediaminetetraacetic acid (EDTA) and the like aminopolycarboxylic acids; and disodium ethylenediaminetetraacetate and the like sodium, potassium and ammonium salts of the aforementioned aminopolycarboxylic acids. Among them, hydroxycarboxylic acids or aminopolycarboxylic acids are desirable from the viewpoint of easy availability, and tartaric acid and EDTA are particularly desirable when cost and the like are synthetically judged.

The chelating agent is used in an amount within the range of 0.0001 mole or more, preferably 0.001 mole or more, more preferably 0.01 mole or more, based on 1 mole of the aluminum reducing agent used in the aforementioned reduction reaction. On the other hand, 50 moles or less, preferably 10 moles or less, more preferably 5 moles or less, further preferably 1 mole or less, still more preferably 0.5 mole or less, is sufficient as the upper limit.

(Contacting Method)

In allowing a water-soluble chelating agent to contact with the 3-amino-1-(2-thienyl)-1-propanols, it is allowed to contact generally as an aqueous solution.

In this connection, when a hydroxycarboxylic acid or the like acidic water-soluble chelating agent is used as the chelating agent, it is desirable to adjust the pH value to 7 or more in advance by adding a base to the aqueous solution.

Regarding the aforementioned base, an inorganic base which can be easily separated at the time of the purification after completion of the reaction is desirable. The aforementioned inorganic base is not particularly limited with the proviso that it dissolves in water, and its illustrative examples include lithium hydroxide, sodium hydroxide, potassium hydroxide and the like alkali metal hydroxides; calcium hydroxide, barium hydroxide and the like alkaline earth metal hydroxides; sodium bicarbonate, potassium bicarbonate and the like alkali metal bicarbonates; calcium bicarbonate, barium bicarbonate and the like alkaline earth metal bicarbonates; sodium carbonate, potassium carbonate and the like alkali metal carbonates; and calcium carbonate, barium carbonate and the like alkaline earth metal carbonates.

Regarding its amount, an amount sufficient for neutralizing the carboxylic acid moiety of the chelating agent may be enough. Also, the inorganic base may be used directly as the solid or in a state of aqueous solution.

In addition, since the 3-amino-1-(2-thienyl)-1-propanols by themselves have high solubility in water, it is desirable to add sodium chloride, sodium sulfate or the like neutral inorganic reagent to the aqueous solution in advance, in order to carry out the extraction with an organic solvent efficiently. Regarding the amount of the aqueous solution to be used, it may be an amount in which the formed aqueous chelate complex of aluminum can be sufficiently dissolved. It is used in an amount of generally from 1 to 100 volumes, preferably from 5 to 30 volumes, based on the 3-amino-1-(2-thienyl)-1-propanols.

The contacting temperature is not particularly limited, but is within the range of generally from 0 to 100° C., preferably from 5 to 70° C.

In addition, since a two layer system is formed in contacting an aqueous solution of water-soluble chelating agent with an organic layer containing the 3-amino-1-(2-thienyl)-1-propanols, it is desirable to carry out sufficient agitation such that the removal of aluminum by the chelating agent can be effectively carried out.

After the aforementioned treatment, an organic solvent is further added to extract the 3-amino-1-(2-thienyl)-1-propanols as occasion demands, the resulting organic layer is concentrated and then they can be isolated and purified by using recrystallization, reprecipitation, column chromatography and the like usual purification techniques.

In spite of the fact that the reduction is carried out using an aluminum reducing agent in the optically active 3-amino-1-(2-thienyl)-1-propanols obtained by the aforementioned method, the aluminum content contained as an aluminum reducing agent-derived impurity is generally 500 ppm or less, preferably 300 ppm or less, more preferably 100 ppm or less, further preferably 50 ppm or less, and particularly preferably 30 ppm or less, so that its removal in subsequent conversion steps can be effected conveniently when the aluminum content is within such a range, and they are therefore desirable compounds as intermediates of pharmaceutical preparations and agricultural chemicals.

Though optical purity of the optically active 3-amino-1-(2-thienyl)-1-propanols obtained by the above method depends on the optical purity of the optically active material amide, it is generally 80% ee or more, preferably 90% ee, and particularly preferably 95% ee, so that the compound of interest can be efficiently obtained without spoiling optical purity of the material.

D) Protection of Hydroxyl Group

In addition, 3-amino-1-(2-thienyl)-1-propanol derivatives useful as intermediates of pharmaceutical preparations and agricultural chemicals can be produced by further protecting the hydroxyl group of said optically active 3-amino-1-(2-thienyl)-1-propanols obtained in the above.

As the aforementioned hydroxyl group protecting method, etherification, silylation, carbonation, sulfonation and the like general hydroxyl group protecting methods can be optionally used, and it is desirable to employ a protection method which is carried out under a basic condition.

For example, a method in which protection of hydroxyl group is carried out by optionally heating 1-fluoronaphthalene or the like halide in dimethylacetamide or the like polar solvent in the presence of 60% sodium hydride or the like base, as described in Japanese Patent No. 2,549,681, can be illustratively exemplified.

Particularly, it is known that a naphthylated product of (1S)-3-methylamino-1-(2-thienyl)-1-propanol is useful as an antidepressant as described in *Journal of Labeled Compounds and Radiopharmaceuticals*, Vol. 36, No. 3, 213–223 (1995).

EXAMPLES

The present invention is described further in detail in the following based on examples, but the invention is not limited to the following examples without overstepping its gist. In the examples, ee indicates enantiomer excess ratio.

Production Example 1

Synthesis of 3-oxo-3-(2-thienyl)propionic acid ethyl ester

A 10.16 g portion of 60% sodium hydride and 78 g of diethyl carbonate were charged using 60 ml of tetrahydrofuran at 24° C. and then the temperature was increased to carry out reflux. At said temperature (79° C.) a solution prepared by dissolving 20 g of 2-acetylthiophene in 20 ml of tetrahydrofuran was added dropwise thereto spending 50 minutes. Thereafter, the mixture was stirred at said temperature for 1 hour and then ice-cooled when the reaction was completed. When the reaction solution was analyzed by a liquid chromatography, the reaction yield was 94%.

A 63 ml portion of 4 N hydrochloric acid aqueous solution was ice-cooled in advance, and the ice-cooled reaction solution was added dropwise thereto in such a manner that the solution temperature was kept at about 10° C. The pH value after the dropwise addition was 6. Next, separation of layers was carried out, and the water layer was further extracted three times with 40 ml of toluene, combined with the first organic layer and washed with 20 ml of saturated brine. Thereafter, this was partially concentrated and then subjected to rectification by attaching a condenser, thereby obtaining 26.9 g (purity 87%, yield 74%) of 3-oxo-(2-thienyl)propionic acid ethyl ester containing the sodium hydride-derived oil component from a fraction of 128 to 130° C. (distillation under 4 mmHg).

$^1$H-NMR (CDCl$_3$) δ 1.27 (t, 3H, J=8 Hz), 3.92 (s, 2H), 4.21 (q, 2H, J=8 Hz), 7.15 (dd, 1H, J=5 Hz, 1 Hz), 7.70 (d, 1H, J=5 Hz), 7.74 (d, 1H, J=1 Hz)

In this connection, the liquid chromatography conditions are as follows.

MCI-Gel ODS 15 cm (mfd. by Mitsubishi Kagaku) 40° C.
Acetonitrile: 50 mM ammonium acetate aqueous solution=50:50 (0.7 ml/min)
Detection wavelength UV 254 nm Production Example 2

Synthesis of 3-oxo-(2-thienyl)propionic acid ethyl ester

A 13.31 g portion of 60% sodium hydride and 56.1 g of diethyl carbonate were charged using 105 ml of tetrahydrofuran at 24° C. and then the temperature was increased to 60° C. At said temperature, a solution prepared by dissolving 30 g of 2-acetylthiophene in 15 ml of tetrahydrofuran was added dropwise thereto spending 20 minutes. Thereafter, the mixture was stirred at said temperature for 1 hour and then ice-cooled when the reaction was completed. When the reaction solution was analyzed by a liquid chromatography under the same conditions of the aforementioned Production Example 1, the reaction yield was 99%.

A 87.4 ml portion of 4 N hydrochloric acid aqueous solution was ice-cooled in advance, and the ice-cooled reaction solution was added dropwise thereto in such a manner that the solution temperature was kept at about 10° C. Since the pH value after the dropwise addition was 1.5, the pH was adjusted to 7 with 25% sodium hydroxide aqueous solution. Separation of layers was carried out, and the water layer was further extracted once with 30 ml of toluene, combined with the first organic layer and washed with 30 ml of 25% brine. The thus obtained organic layer was concentrated to a pressure of 50 mmHg. Next, in order to separate the oil component originated from NaH, 30 ml of acetonitrile and 30 ml of heptane were added at 25° C. and stirred for 30 minutes, and then the heptane layer was separated to remove the oil component. By concentrating the acetonitrile layer (under a pressure of 5 mmHg), 46.3 g (purity 92%, yield 90%) of 3-oxo-3-(2-thienyl)propionic acid ethyl ester was obtained.

Production Example 3

Synthesis of 3-oxo-3-(2-thienyl)propionic acid ethyl ester

A 0.254 g portion of 60% sodium hydride and 1.95 g of diethyl carbonate were charged using 1.0 ml of tetrahydrofuran at 24° C. and then the temperature was increased to carry out reflux. At said temperature (79° C.) a solution prepared by dissolving 0.5 g of 2-acetylthiophene in 1 ml of tetrahydrofuran was added dropwise thereto spending 15 minutes. Thereafter, the mixture was stirred at said temperature for 1 hour, and when the reaction was completed, the reaction solution was analyzed by a liquid chromatography under the same conditions of the aforementioned Production Example 1 to find that the reaction yield was 89%.

Reference Example 1

A 0.254 g portion of 60% sodium hydride was charged using 1.5 ml of tetrahydrofuran at 24° C. At said temperature (79° C.), a solution prepared by dissolving 1.95 g of diethyl carbonate and 0.5 g of 2-acetylthiophene in 1 ml of tetrahydrofuran was added dropwise thereto spending 15 minutes. Thereafter, the mixture was stirred at said temperature for 1 hour, and when the reaction was completed, the reaction solution was analyzed by a liquid chromatography under the same conditions of the aforementioned Production Example 1 to find that the reaction yield was 83%.

Production Example 4

Synthesis of 3-oxo-3-(2-thienyl)propionic acid ethyl ester

A 71.1 g (0.63 mol) portion of tert-butoxy potassium was added to 194.7 g (1.65 mol) of diethyl carbonate at 60 to 65° C. and stirred at 60 to 65° C. for 1 hour, and then 180 ml of toluene solution containing 50 g (0.40 mol) of 2-acetylthiophene was added dropwise thereto at 75 to 80° C. and stirred at 75 to 80° C. for 2 hours. The reaction solution was cooled down to room temperature, mixed with 725 g of water, extracted with 600 ml of ethyl acetate, washed with saturated brine, concentrated and then distilled under a reduced pressure to obtain 65.2 g of 3-oxo-3-(2-thienyl)propionic acid ethyl ester (yield 83%).

Production Example 5

Synthesis of
N-methyl-3-oxo-3-(2-thienyl)propionamide

A 9.8 g (126.26 mmol) portion of 40% methylamine/methanol solution was added to 20 ml of methanol solution containing 5 g (25.25 mmol) of 3-oxo-3-(2-thienyl)propionic acid ethyl ester obtained in Reference Example 1 and stirred at room temperature for 19 hours. After the reaction, the solvent and excess methylamine were evaporated under a reduced pressure to obtain 4.6 g of crystals of N-methyl-3-oxo-3-(2-thienyl)propionamide.

$^1$H-NMR (CDCl$_3$) δ 2.85, 2.87 (s, 3H, methylamido group-derived rotational isomer), 3.90 (s, 2H), 7.15 (m, 1H), 7.17 (dd, 1H J=4.8 Hz, 3.8 Hz), 7.74 (dd, 1H J=4.8 Hz, 1.0 Hz), 7.83 (dd, 1H J=3.8 Hz, 1.0 Hz)

Example 1

Synthesis of (S)-3-hydroxy-3-(2-thienyl)propionic acid ethyl ester

A 30 ml-capacity flask was charged with 2.34 g (23.11 mmol) of triethylamine and 3 ml of dry N,N-dimethylformamide (to be referred to as DMF hereinafter), next, 1.01 g (21.90 mmol) of formic acid and 4.02 g (20.28 mmol) of the 3-oxo-3-(2-thienyl)propionic acid ethyl ester obtained in Production Example 4 were added thereto under ice-cooling, and finally, 6.6 mg (0.01 mmol) of RuCl(p-cymene)[(S,S)-N-p-toluenesulfonyl-1,2-diphenylethylenediamine] (to be referred to as RuCl(p-cymene)(SS-TsDPEN) hereinafter) was added thereto, and the mixture was stirred at 50° C. for 42 hours. After the reaction, this was mixed with 2 ml of water under ice-cooling, adjusted to pH 2 by adding 10% hydrochloric acid, extracted with ethyl acetate and washed with saturated brine, saturated sodium bicarbonate and saturated brine in that order, the solvent was concentrated under a reduced pressure and then the residue was purified by a silica gel column chromatography to obtain 3.83 g of (S)-3-hydroxy-3-(2-thienyl)propionic acid ethyl ester (yield 94%).

In addition, its optical purity was determined by a high performance liquid chromatography under the following conditions to find that it was 97.5% ee.

Chiralcel OD (mfd. by Daicel) 35° C.
n-Hexane: 2-propanol=90:10 (1 ml/min)
Detection wavelength UV 230 nm Example 2

Synthesis of (S)-3-hydroxy-3-(2-thienyl)propionic acid ethyl ester

A 200 ml-capacity flask was charged with 16.71 g (165 mmol) of triethylamine and 20 ml of dry DMF, next, 7.20 g (156 mmol) of formic acid and 28.57 g (144 mmol) of the 3-oxo-3-(2-thienyl)propionic acid ethyl ester obtained in Production Example 4 were added thereto under ice-cooling, and finally, 45.8 mg (0.072 mmol) of RuCl(p-cymene)(SS-TsDPEN) was added thereto, and the mixture was stirred at 50° C. for 40 hours. After the reaction, this was mixed with 14 ml of water under ice-cooling, adjusted to pH 2 by adding 10% hydrochloric acid, extracted with ethyl acetate and washed with saturated brine, saturated sodium bicarbonate and saturated brine in that order, the solvent was concentrated under a reduced pressure and then the residue was distilled under a reduced pressure to obtain 26.53 g of (S)-3-hydroxy-3-(2-thienyl)propionic acid ethyl ester (yield 92%).

In addition, its optical purity was determined in the same manner as in Example 1 to find that it was 97.5% ee.

Example 3

Synthesis of optically active
3-hydroxy-3-(2-thienyl)propionic acid ethyl ester
using microorganism An aqueous solution comprising a composition of 2% glucose, 1% yeast extract, 1% polypeptone, and 0.6% malt extract was used as the medium, and *Filobasidium unigutulatum* IFO 0699 was inoculated into this and aerobically cultured at 28° C. for 24 hours. After completion of the culturing, the culture medium (1 ml) was collected and centrifuged to isolate the cells. 3-Oxo-3-(2-thienyl)propionic acid ethyl ester to be used as the substrate was synthesized in accordance with the method described in EP-A-751427. Said cells were suspended in 200 µl of a reaction solution comprising 100 mM glucose, 0.24% 3-oxo-3-(2-thienyl)propionic acid ethyl ester, 0.01% NADH, 0.01% NADPH and 100 mM Tris-HCl buffer (pH 7.5) and allowed to undergo the reaction at 30° C. on a shaker. After 18 hours of the commencement of the reaction, 800 µl of 2-propanol was added thereto, the cells were removed by centrifugation, and then a sample of the supernatant was analyzed by HPLC. The analysis was carried out under the following conditions using Chiralpak AD-RH (mfd. by Daicel) as the HPLC column.

Temperature: 35° C.
Detector: UV detector (245 nm)
Eluent: 70% 10 mM phosphate buffer (pH 6.0), 30% acetonitrile
Flow rate: 1 ml/min Racemic bodies of 3-hydroxy-0.3-(2-thienyl)propionic acid ethyl ester were synthesized by the method of Bieber et al. (*J. Organic Chem.*, vol. 62, no. 26, pp. 9061-9064, 1997) and used as the standards to carry out the analysis under the aforementioned conditions, and by analyzing optical rotatory power of the thus obtained two peaks (peaks having retention times of 9.3 minutes and 10.5 minutes in FIG. 1), peaks of (R)-form (retention time 9.3 minutes in FIG. 1) and (S)-form of 3-hydroxy-3-(2-thienyl)propionic acid ethyl ester (retention time 10.5 minutes in FIG. 1) were identified. When the reaction solution was analyzed, it was confirmed that a peak was formed at the same detection time of (S)-3-hydroxy-3-(2-thienyl)propionic acid ethyl ester.

Figure 2:
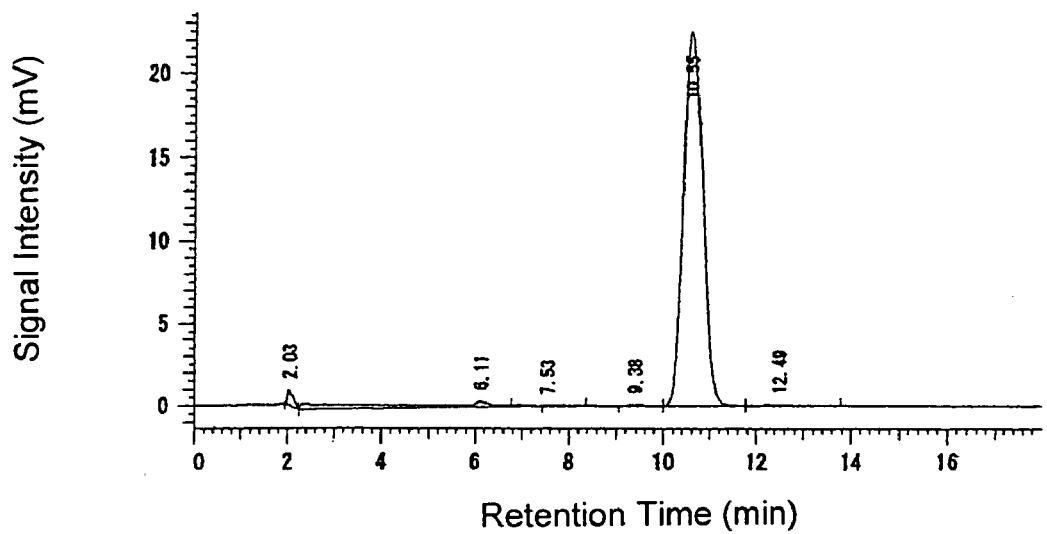
FIG. 2 is a chart showing a result in which (S)-form 3-hydroxy-3-(2-thienyl)propionic acid ethyl ester formed by a microbial cell reaction was fractionated by HPLC and again analyzed by HPLC. The retention time (minute) is plotted as abscissa, and the signal strength (mV) as ordinate.
Figure 3:
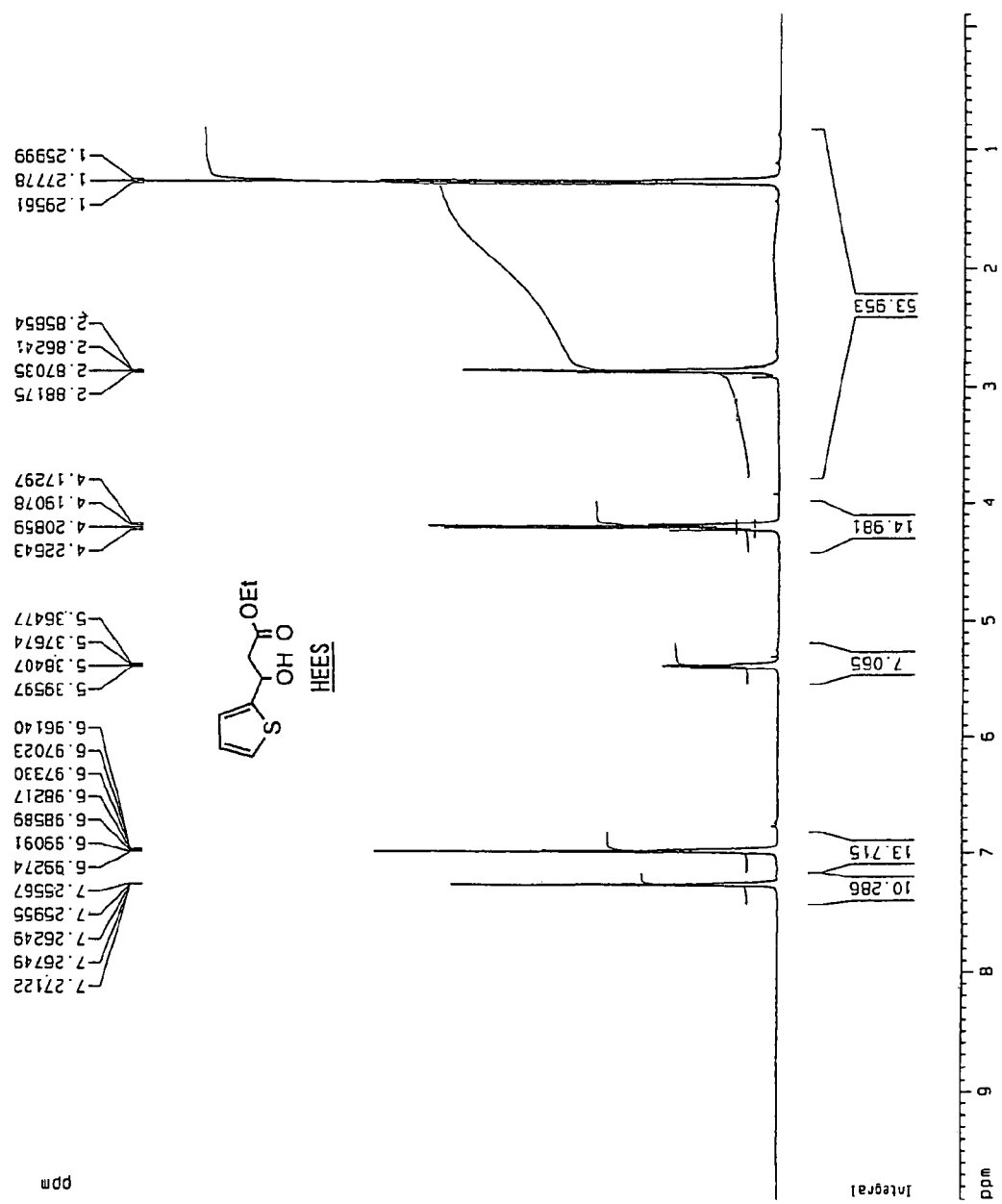
FIG. 3 is a chart showing a result in which (S)-form 3-hydroxy-3-(2-thienyl)propionic acid ethyl ester formed by a microbial cell reaction was fractionated by HPLC and analyzed by NMR.

Also, a substance considered to be (S)-3-hydroxy-3-(2-thienyl)propionic acid ethyl ester (FIG. 2) obtained by fractionating and purifying the peak separated under the aforementioned HPLC conditions was analyzed by NMR (FIG. 3).

$^1$H-NMR (CDCl$_3$) δ 1.27 (t, 3H, J=7 Hz), 2.86 (d, 1H, J=2 Hz), 2.87 (d, 1H, J=5 Hz), 4.20 (q, 2H, J=7 Hz), 5.38 (m, 1H), 6.98 (m, 2H), 7.26 (d, 1H, J=5 Hz)

m/z: 200

In addition, it was determined by the NMR-aided new Mosher method (*Journal of Synthetic Organic Chemistry* (written in Japanese), vol. 51, pp. 462–470, 1993) that its absolute configuration is (S)-form. Based on the above, the substance formed by the aforementioned reaction was iden tified as (S)-3-hydroxy-3-(2-thienyl)propionic acid ethyl ester.

Concentration of the formed (S)-3-hydroxy-3-(2-thienyl)propionic acid ethyl ester was 729 mg/l, and its optical purity was 99.5% ee.

The same test was carried out on other various microorganisms, with the results shown in Table 1. Regarding (R)-3-hydroxy-3-(2-thienyl)propionic acid ethyl ester, it can also be identified by carrying out NMR analysis in the same manner as described in the foregoing.

TABLE 1

| Strain | Product conc. (mg/L) | Optical Purity of product (% e. e.) | |
|---|---|---|---|
| *Arthrobacter atrocyaneus* JCM1329 | 9.77 | 4.53 | R |
| *Candida albicans* IFO0759 | 1580 | 56.2 | R |
| *Candida holmii* IFO1629 | 1250 | 55.2 | R |
| *Candida parapsilosis* CBS604 | 2.63 | >99.8 | R |
| *Candida parapsilosis* IFO1396 | 5.91 | 79.4 | R |
| *Candida vaccinii* JCM9446 | 2190 | 39.2 | R |
| *Candida valida* IFO10318 | 406 | 87.2 | R |
| *Cryptococcus humicolus* IFO10250 | 389 | 58.1 | R |
| *Kloeckera corticis* IFO0631 | 446 | 49.4 | R |
| *Kloeckera corticis* IFO1097 | 40.3 | 5.31 | R |
| *Kodamaea ohmeri* IFO0158 | 839 | 1.10 | R |
| *Leucosporidium scottii* IFO1212 | 723 | 20.7 | R |
| *Metschnikowia bicuspidata* var. *californica* IFO10787 | 1680 | 42.6 | R |
| *Metschnikowia krissii* IFO1677 | 300 | 22.9 | R |
| *Metschnikowia pulcherrima* IAM12196 | 626 | 44.5 | R |
| *Metschnikowia pulcherrima* IAM12197 | 247 | 59.2 | R |
| *Metschnikowia pulcherrima* IFO0863 | 393 | 96.6 | R |
| *Metschnikowia pulcherrima* IFO10796 | 684 | 64.8 | R |
| *Metschnikowia pulcherrima* IFO1407 | 833 | 32.4 | R |
| *Metschnikowia pulcherrima* IFO1678 | 1810 | 46.4 | R |
| *Paenibacillus alvei* IFO3343 | 438 | >99.8 | R |
| *Pichia angophorae* IFO10016 | 781 | 88.5 | R |
| *Pichia bovis* IFO0872 | 922 | 98.6 | R |
| *Pichia cactophila* JCM1830 | 889 | 48.7 | R |
| *Pichia chambardii* IFO1274 | 259 | 21.2 | R |
| *Pichia fluxuum* JCM3646 | 323 | 19.9 | R |
| *Pichia japonica* IFO10721 | 1370 | 51.4 | R |
| *Pichia lynferdii* IFO10724 | 1310 | 73.4 | R |
| *Pichia manshurica* IFO0181 | 628 | 22.2 | R |
| *Pichia manshurica* IFO0864 | 1110 | 76.5 | R |
| *Pichia misumaiensis* IFO10221 | 296 | 1.37 | R |
| *Pichia naganishii* IFO1670 | 1120 | 94.5 | R |
| *Pichia nakasei* JCM1699 | 285 | 42.3 | R |
| *Pichia nakazawae* var. *akitaensis* JCM10738 | 96.6 | 12.0 | R |
| *Pichia nakazawae* var. *nakazawae* JCM7529 | 402 | 6.48 | R |
| *Pichia philogaea* JCM10739 | 580 | 50.6 | R |
| *Pichia rhodanensis* JCM3649 | 72.8 | 78.9 | R |
| *Pichia silvicola* JCM3627 | 33.2 | 71.6 | R |
| *Pichia subpelliculosa* IFO0808 | 352 | 33.5 | R |
| *Pichia toletana* IFO1275 | 188 | 28.0 | R |
| *Pichia trehalophila* JCM3651 | 120 | 41.8 | R |
| *Pichia triangularis* JCM2379 | 192 | 97.7 | R |
| *Pichia veronae* IFO1667 | 390 | 14.3 | R |
| *Saccharomycs exiguus* IFO1170 | 1930 | 79.2 | R |
| *Ambrosiozyma arabrosiae* IFO10835 | 179 | 87.1 | S |
| *Ambrosiozyma cicatricosa* JCM7598 | 481 | 75.0 | S |
| *Ambrosiozyma monospora* IFO1965 | 318 | >99.8 | S |
| *Ambrosiozyma monospora* JCM7599 | 492 | 66.5 | S |
| *Ambrosiozyma philentoma* JCM7600 | 193 | >99.8 | S |
| *Ambroziozyma platypodis* IFO1471 | 1330 | 11.8 | S |
| *Brettanomyces anomalus* IFO0627 | 344 | >99.8 | S |
| *Brettanomyces bruxellensis* IFO629 | 739 | 99.3 | S |
| *Brettanomyces bruxellensis* IFO0797 | 305 | 98.9 | S |
| *Brettanomyces naardenensis* IFO1588 | 2360 | 92.5 | S |
| *Brevibacterium sacchrolyticum* ATCC14066 | 1120 | >99.8 | S |
| *Bullera pseudoalba* JCM5290 | 280 | >99.8 | S |
| *Bullera unica* JCM8932 | 178 | >99.8 | S |
| *Candia lambica* JCM9557 | 50.6 | >99.8 | S |
| *Candida boidinii* IFO10035 | 731 | 96.5 | S |
| *Candida boidinii* IFO10240 | 1670 | 65.2 | S |
| *Candida boidinii* IFO10329 | 1270 | 90.2 | S |
| *Candida boidinii* IFO10574 | 1610 | 74.0 | S |
| *Candida cylindracea* ATCC14830 | 101 | 86.8 | S |
| *Candida deserticola* IFO10232 | 276 | >99.8 | S |
| *Candida famata* ATCC20850 | 26.3 | 77.8 | S |
| *Candida famata* IFO0856 | 73.6 | >99.8 | S |
| *Candida glabrata* ATCC15126 | 278 | 39.2 | S |
| *Candida glabrata* IFO0005 | 2.16 | 2.57 | S |
| *Candida glabrata* IFO0622 | 560 | 67.2 | S |

TABLE 1-continued

| Strain | Product conc. (mg/L) | Optical Purity of product (% e. e.) | |
|---|---|---|---|
| Candida glaebosa IFO1353 | 152 | >99.8 | S |
| Candida globosa IFO0953 | 160 | >99.8 | S |
| Candida gropengiesseri IFO0659 | 131 | 10.5 | S |
| Candida intermedia IFO0761 | 1020 | 1.11 | S |
| Candida krusei IFO0201 | 496 | >99.8 | S |
| Candida krusei IFO1162 | 440 | >99.8 | S |
| Candida krusei IFO1664 | 258 | 91.3 | S |
| Candida krusei JCM1608 | 384 | >99.8 | S |
| Candida krusei JCM1609 | 329 | >99.8 | S |
| Candida krusei JCM1712 | 408 | >99.8 | S |
| Candida krusei JCM2284 | 379 | >99.8 | S |
| Candida krusei JCM2341 | 356 | >99.8 | S |
| Candida magnoliae IFO0705 | 2070 | 31.4 | S |
| Candida maitosa IFO1977 | 384 | 70.3 | S |
| Candida melinii IFO0747 | 507 | 84.7 | S |
| Candida melinii JCM2276 | 57.7 | 28.2 | S |
| Candida molischiana IFO10296 | 61.7 | 86.8 | S |
| Candida norvegensis JCM2307 | 349 | 90.7 | S |
| Candida parapsilosis IFO0585 | 24.8 | >99.8 | S |
| Candida pini IFO1327 | 370 | 99.2 | S |
| Candida quercuum IFO1576 | 146 | >99.8 | S |
| Candida rugosa IFO0591 | 3.27 | >99.8 | S |
| Candida sake IFO0435 | 484 | 55.3 | S |
| Candida solani IFO0762 | 660 | 91.3 | S |
| Candida tropicalis IFO0006 | 423 | 89.6 | S |
| Candida tropicalis IFO0199 | 279 | 91.3 | S |
| Candida tropicalis IFO0618 | 261 | 95.3 | S |
| Candida tropicalis IFO1647 | 62.6 | 70.3 | S |
| Candida utilis IAM4961 | 181 | 94.1 | S |
| Candida utilis IFO0396 | 238 | 95.1 | S |
| Candida vartiovaarae JCM3759 | 20.4 | 76.3 | S |
| Candida zeylanoides CBS6408 | 111 | 91.3 | S |
| Candida zeylanoides IFO10325 | 162 | 72.8 | S |
| Candida zeylanoides JCM1627 | 169 | 62.6 | S |
| Citeromyces matritensis IFO0651 | 165 | 94.1 | S |
| Citeromyces matritensis IFO0954 | 67.3 | >99.8 | S |
| Corynebacterium acetoacidophilum ATCC13870 | 1460 | >99.8 | S |
| Corynebacterium ammoniagenes JCM1305 | 1190 | >99.8 | S |
| Corynebacterium flavescens JCM1305 | 889 | >99.8 | S |
| Corynebacterium glutamicum ATCC13032 | 1260 | >99.8 | S |
| Corynebacterium glutamicum ATCC13826 | 1350 | >99.8 | S |
| Corynebacterium glutamicum ATCC13869 | 1060 | >99.8 | S |
| Corynebacterium variabile JCM2154 | 637 | >99.8 | S |
| Cryptococcus aerius IFO0377 | 1210 | >99.8 | S |
| Cryptococcus aerius IFO1322 | 311 | >99.8 | S |
| Cryptococcus alubidus IFO0378 | 619 | 99.1 | S |
| Cryptococcus alubidus IFO0612 | 202 | 98.7 | S |
| Cryptococcus cellulolyticus JCM9707 | 175 | >99.8 | S |
| Cryptococcus curvatus IFO1159 | 115 | >99.8 | S |
| Cryptococcus heveanensis JCM3693 | 374 | >99.8 | S |
| Cryptococcus laurentii DSM70766 | 1020 | >99.8 | S |
| Cryptococcus laurentii IFO1898 | 2020 | 99.2 | S |
| Cryptococcus laurentii var. laurentii CBS2174 | 444 | 98.7 | S |
| Cryptococcus laurentii var. laurentii CBS5297 | 266 | >99.8 | S |
| Cryptococcus laurentii var. laurentii CBS5746 | 228 | >99.8 | S |
| Cryptococcus laurentii var. laurentii CBS7140 | 89.4 | >99.8 | S |
| Cryptococcus luteolus IFO0411 | 311 | 98.4 | S |
| Cryptococcus magnus JCM9038 | 693 | >99.8 | S |
| Cryptococcus terreus IFO0727 | 1930 | >99.8 | S |
| Cryptococcus terreus JCM8975 | 537 | >99.8 | S |
| Cryptococcus yarrowii JCM8232 | 61.4 | >99.8 | S |
| Cystofilobasidium bisporidii JCM9050 | 77.3 | >99.8 | S |
| Cystofilobasidium capitatum JCM3793 | 125 | >99.8 | S |
| Cystofilobasidium infirmominiatum JCM3797 | 220 | >99.8 | S |
| Cystofilobasidium infirmominiatum JCM8159 | 90.7 | >99.8 | S |
| Debaryomyces hansenii var. fabryi JCM1441 | 186 | >99.8 | S |
| Debaryomyces hansenii var. fabryi JCM2104 | 135 | >99.8 | S |
| Debaryomyces hansenii var. hansenii IFO0032 | 186 | >99.8 | S |
| Debaryomyces hansenii var. hansenii IFO0034 | 160 | >99.8 | S |
| Debaryomyces hansenii var. hansenii IFO0060 | 222 | >99.8 | S |
| Debaryomyces hansenii var. hansenii IFO0855 | 347 | 91.6 | S |
| Debaryomyces hansenii var. hansenii JCM1521 | 57.8 | >99.8 | S |
| Debaryomyces hansenii var. hansenii JCM2192 | 46.5 | >99.8 | S |
| Debaryomyces hansenii var. hansenii JCM2194 | 71.3 | >99.8 | S |
| Debaryomyces hansenii var. hansenii JCM2196 | 123 | 94.6 | S |
| Debaryomyces maramus JCM1528 | 85.8 | >99.8 | S |

TABLE 1-continued

| Strain | Product conc. (mg/L) | Optical Purity of product (% e. e.) | |
|---|---|---|---|
| Debaryomyces melissophilus JCM1707 | 24.2 | >99.8 | S |
| Debaryomyces polymorphus JCM3647 | 88.9 | 8.50 | S |
| Debaryomyces pseudopolymorphus JCM3652 | 131 | 75.7 | S |
| Debaryomyces robertsiae IFO1277 | 180 | 92.0 | S |
| Debaryomyces vanrijiae var. vanrijiae JCM3657 | 295 | 96.4 | S |
| Debaryomyces vanrijiae var. yarrowii JCM6190 | 132 | 39.4 | S |
| Dekkera bruxellensis CBS2796 | 562 | 99.2 | S |
| Endomyces decipiens IFO0102 | 347 | 96.9 | S |
| Exophiala dermatitidis IFO6421 | 119 | 77.0 | S |
| Exophiala dermatitidis IFO8193 | 169 | 55.5 | S |
| Fellomyces fuzhouensis IFO10374 | 36.3 | >99.8 | S |
| Filobasidium capsuligenum IFO1119 | 88.3 | 83.6 | S |
| Filobasidium capsuligenum IFO1185 | 1040 | 99.5 | S |
| Filobasidium elegans IFO10881 | 672 | 98.5 | S |
| Filobasidium floriforme IFO10886 | 804 | 97.8 | S |
| Filobasidium floriforme IFO1603 | 702 | 98.5 | S |
| Filobasidium globisporum IFO10887 | 627 | 97.9 | S |
| Filobasidium uniguttulatum IFO0699 | 729 | 99.5 | S |
| Hanseniaspora guilliermondii IFO1411 | 26.7 | 83.5 | S |
| Hanseniaspora uvarum IFO1755 | 20.1 | 52.8 | S |
| Holtermannia corniformis JCM1743 | 725 | >99.8 | S |
| Issatchenkia orientalis IFO1279 | 410 | 98.6 | S |
| Issatchenkia scutulata var. exigua JCM1829 | 210 | >99.8 | S |
| Issatchenkia scutulata var. scutulata JCM1828 | 132 | >99.8 | S |
| Issatchenkia terricola IFO0933 | 249 | >99.8 | S |
| Issatchenkia terricola IFO1907 | 466 | >99.8 | S |
| Kloeckera apiculata IFO0865 | 10.6 | 41.9 | S |
| Kloeckera japonica IFO0151 | 59.6 | 91.2 | S |
| Kluyveromyces lactis var. lactis IFO1267 | 878 | 77.0 | S |
| Kluyveromyces marxianus CBS834 | 611 | 94.1 | S |
| Kluyveromyces thermotolerans IFO0662 | 3120 | 2.94 | S |
| Kluyveromyces thermotolerans IFO1050 | 1240 | 98.2 | S |
| Kluyveromyces thermotolerans IFO1674 | 2320 | 40.5 | S |
| Kluyveromyces thermotolerans IFO1779 | 1560 | 86.7 | S |
| Kluyveromyces thermotolerans IFO1780 | 1690 | 94.6 | S |
| Kluyveromyces thermotolerans IFO1985 | 2040 | 15.3 | S |
| Komagataella pastoris ATCC28485 | 221 | 85.5 | S |
| Komagataella pastoris IFO0948 | 111 | 58.9 | S |
| Komagataella pastoris IFO1013 | 454 | 65.3 | S |
| Lipomyces tetrasporus IFO10391 | 47.5 | 89.0 | S |
| Lodderomyces elongisporus IFO1676 | 32.3 | 64.9 | S |
| Metschnikowia agaves IFO10860 | 331 | 97.6 | S |
| Metschnikowia australis IFO10783 | 301 | 94.9 | S |
| Metschnikowia bicuspidata var. bicuspidata IFO1408 | 1200 | 15.8 | S |
| Metschnikowia bicuspidata var. chathamia IFO10785 | 888 | 4.66 | S |
| Metschnikowia gruessii IFO10788 | 672 | 31.0 | S |
| Metschnikowia hawaiiensis IFO10791 | 175 | 96.7 | S |
| Metschnikowia lunata IFO1605 | 1020 | 92.5 | S |
| Metschnikowia reukaufii IFO10798 | 84.6 | 35.1 | S |
| Metschnikowia reukaufii IFO1679 | 87.0 | 44.0 | S |
| Metschnikowia reukaufii JCM2279 | 1370 | 54.9 | S |
| Metschnikowia sp. IFO1406 | 142 | 75.2 | S |
| Metschnikowia zobellii IFO10800 | 1030 | 33.8 | S |
| Metschnikowia zobellii IFO1680 | 2070 | 19.0 | S |
| Ogataea minuta var. minuta IFO0975 | 654 | 41.2 | S |
| Ogataea minuta var. nonfermentans IFO1473 | 267 | 81.1 | S |
| Ogataea polymorpha IFO1475 | 359 | 83.7 | S |
| Pichia amylophila JCM1702 | 62.0 | 52.7 | S |
| Pichia anomala IFO0118 | 419 | 11.8 | S |
| Pichia augusta ATCC26012 | 373 | 66.0 | S |
| Pichia barkeri IFO10714 | 636 | >99.8 | S |
| Pichia besseyi JCM1706 | 455 | >99.8 | S |
| Pichia bimundalis JCM3591 | 62.4 | 2.71 | S |
| Pichia bispora JCM3590 | 8.65 | 9.57 | S |
| Pichia canadensis JCM3597 | 183 | 52.1 | S |
| Pichia castillae JCM10733 | 412 | >99.8 | S |
| Pichia delftensis IFO10715 | 591 | 88.8 | S |
| Pichia deserticola IFO10716 | 950 | >99.8 | S |
| Pichia dryadoides IFO1820 | 441 | 98.7 | S |
| Pichia euphorbiiphila IFO10717 | 572 | 75.1 | S |
| Pichia fabianii JCM3601 | 123 | 93.9 | S |
| Pichia fermentans JCM2189 | 100 | >99.8 | S |
| Pichia hampshirensis IFO10719 | 332 | >99.8 | S |
| Pichia heedii JCM1833 | 30.9 | >99.8 | S |
| Pichia heimii IFO1686 | 39.5 | >99.8 | S |
| Pichia inositovora JCM10736 | 92.8 | 90.0 | S |

TABLE 1-continued

| Strain | Product conc. (mg/L) | Optical Purity of product (% e. e.) | |
|---|---|---|---|
| *Pichia jadinii* JCM3617 | 91.8 | >99.8 | S |
| *Pichia kluyveri* var. *cephalocereana* IFO10722 | 526 | >99.8 | S |
| *Pichia kluyveri* var. *eremophila* IFO10723 | 286 | >99.8 | S |
| *Pichia kluyveri* var. *kluyveri* IFO1165 | 282 | 98.4 | S |
| *Pichia media* JCM10737 | 40.6 | 60.3 | S |
| *Pichia methanolica* ATCC58403 | 431 | 67.4 | S |
| *Pichia methylivora* IFO10705 | 55.6 | 79.7 | S |
| *Pichia mexicana* JCM1835 | 272 | 97.6 | S |
| *Pichia meyerae* IFO10727 | 337 | 94.8 | S |
| *Pichia mississippiensis* JCM1703 | 75.3 | >99.8 | S |
| *Pichia norvegensis* IFO1694 | 352 | 91.6 | S |
| *Pichia onychis* IFO1682 | 147 | 82.1 | S |
| *Pichia petersonii* IFO1372 | 495 | 97.1 | S |
| *Pichia pijperi* IFO1290 | 300 | 92.4 | S |
| *Pichia populi* IFO10729 | 184 | 81.1 | S |
| *Pichia pseudocactophila* IFO10730 | 997 | 93.4 | S |
| *Pichia quercuum* JCM3659 | 89.2 | 67.4 | S |
| *Pichia rabaulensis* IFO1643 | 135 | 88.9 | S |
| *Pichia salicaria* JCM3653 | 65.5 | 91.6 | S |
| *Pichia scolyti* JCM3654 | 16.8 | >99.8 | S |
| *Pichia segobiensis* JCM10740 | 105 | 90.4 | S |
| *Pichia spartinae* JCM10741 | 198 | >99.8 | S |
| *Pichia strasburgensis* JCM3660 | 240 | >99.8 | S |
| *Pichia sydowiorum* JCM9455 | 197 | 55.8 | S |
| *Pichia tannicola* JCM8120 | 804 | 80.4 | S |
| *Pichia wickerhamii* IFO1278 | 867 | 79.4 | S |
| *Rhodotorula aurantiaca* IFO0754 | 142 | 98.3 | S |
| *Rhodotorula fragaria* JCM3930 | 48.9 | >99.8 | S |
| *Rhodotorula glutinis* var. *dairenensis* IFO0415 | 38.2 | >99.8 | S |
| *Rhodotorula graminis* JCM3775 | 27.4 | >99.8 | S |
| *Rhodotorula hordea* JCM3932 | 154 | 87.8 | S |
| *Rhodotorula hylophila* JCM1805 | 223 | 95.0 | S |
| *Rhodotorula ingeniosa* JCM9031 | 257 | >99.8 | S |
| *Rhodotorula javanica* JCM9032 | 149 | >99.8 | S |
| *Rhodotorula minuta* IFO0387 | 1380 | 99.5 | S |
| *Rhodotorula minuta* IFO0715 | 458 | >99.8 | S |
| *Rhodotorula minuta* IFO0920 | 1040 | 97.5 | S |
| *Rhodotorula minuta* JCM3776 | 77.4 | >99.8 | S |
| *Rhodotorula mucilaginosa* IFO0870 | 327 | >99.8 | S |
| *Rhodotorula muscorum* JCM1697 | 126 | >99.8 | S |
| *Rhodotorula philyla* JCM3933 | 471 | 91.0 | S |
| *Rhodotorula pustula* JCM3934 | 39.5 | >99.8 | S |
| *Saccharomyces cerevisiae* IFO0305 | 185 | 84.7 | S |
| *Saccharomyces cerevisiae* IFO0565 | 996 | 80.0 | S |
| *Saccharomyces cerevisiae* JCM1818 | 450 | 86.6 | S |
| *Saccharomycodes ludwigii* IFO0798 | 588 | 74.3 | S |
| *Saccharomycopsis fibuligera* IFO0105 | 885 | 71.5 | S |
| *Saccharomycopsis fibuligera* IFO1744 | 2300 | 99.8 | S |
| *Saccharomycopsis malanga* IFO1710 | 287 | 95.0 | S |
| *Saccharomycopsis schoenii* IFO1579 | 697 | >99.8 | S |
| *Saccharomycopsis synnaedendra* IFO1604 | 253 | >99.8 | S |
| *Saitoella complicata* IAM12963 | 61.4 | >99.8 | S |
| *Schizoblastosporion chiloense* IFO10841 | 348 | 54.3 | S |
| *Schizosaccharomyces japonicus* JCM8263 | 323 | 95.1 | S |
| *Schizosaccharomyces octosporus* IFO10373 | 121 | >99.8 | S |
| *Schizosaccharomyces pombe* IFO1628 | 425 | 96.4 | S |
| *Schizosaccharomycs pombe* IFO0344 | 639 | 99.2 | S |
| *Sirobasidium magnum* JCM6876 | 207 | >99.8 | S |
| *Sporidiobolus johnsonii* IFO6903 | 738 | 97.2 | S |
| *Sterigmatomyces halophilus* IFO1488 | 506 | >99.8 | S |
| *Sterigmatosporidium polymorphum* JCM6902 | 10.8 | >99.8 | S |
| *Torulaspora delbrueckii* CBS1146 | 561 | 52.5 | S |
| *Tremella aurantia* JCM11327 | 436 | 98.4 | S |
| *Tremella encephala* JCM11329 | 97.7 | >99.8 | S |
| *Tremella foliacea* JCM11330 | 427 | 86.4 | S |
| *Trichosporon domesticum* JCM9580 | 414 | >99.8 | S |
| *Trichosporon laibachii* JCM9934 | 511 | >99.8 | S |
| *Trichosporon montevideense* JCM9937 | 562 | >99.8 | S |
| *Trichosporon mucoides* JCM9939 | 178 | >99.8 | S |
| *Trichosporon sp.* IFO116 | 208 | 83.9 | S |
| *Trichosporonoides megachiliensis* CBS567.85 | 1090 | 92.9 | S |
| *Trichosporonoides oedocephalis* CBS568.85 | 1060 | 89.6 | S |
| *Trigonopsis variabilis* CBS1040 | 37.8 | 70.2 | S |
| *Trigonopsis variabilis* CBS4069 | 120 | 88.4 | S |
| *Trigonopsis variabillis* IFO0671 | 6.75 | >99.8 | S |
| *Waltomyces lipofer* IFO1288 | 188 | 71.4 | S |

TABLE 1-continued

| Strain | Product conc. (mg/L) | Optical Purity of product (% e. e.) | |
|---|---|---|---|
| Wickerhamiella domercqiae IFO1857 | 9.59 | >99.8 | S |
| Williopsis californica JCM3600 | 91.6 | >99.8 | S |
| Williopsis californica JCM3605 | 70.9 | >99.8 | S |
| Williopsis mucosa JCM6809 | 100 | 97.5 | S |
| Williopsis saturnus var. mrakii JCM3614 | 329 | 96.1 | S |
| Williopsis saturnus var. sargentensis IFO1826 | 319 | 99.1 | S |
| Williopsis saturnus var. saturnus IFO10697 | 326 | 97.9 | S |
| Williopsis saturnus var. saturnus JCM1826 | 339 | 98.0 | S |
| Williopsis saturnus var. saturnus JCM3594 | 150 | 97.6 | S |
| Williopsis saturnus var. saturnus JCM3595 | 131 | 96.2 | S |
| Williopsis saturnus var. saturnus JCM3596 | 68.0 | 67.0 | S |
| Williopsis saturnus var. saturnus JCM3623 | 182 | 98.6 | S |
| Williopsis saturnus var. saturnus JCM3624 | 206 | 98.4 | S |
| Williopsis saturnus var. saturnus JCM9398 | 644 | 98.1 | S |
| Williopsis saturnus var. suaveolens IFO10698 | 153 | 97.7 | S |
| Williopsis saturnus var. subsufficiens JCM3625 | 489 | 91.1 | S |
| Williopsis saturnus var. subsufficiens JCM3626 | 363 | 91.4 | S |
| Yamadazyma farinosa IFO0193 | 25.3 | 24.6 | S |
| Yamadazyma farinosa IFO10061 | 82.1 | 60.0 | S |
| Yamadazyma haplophila IFO0947 | 573 | 94.8 | S |
| Yarrowia lipolytica ATCC8661 | 52.8 | >99.8 | S |
| Yarrowia lipolytica IFO1209 | 87.5 | >99.8 | S |
| Yarrowia lipolytica IFO1548 | 41.2 | 94.9 | S |

Example 4

Synthesis of (3S)-3-hydroxy-N-methyl-3-(2-thienyl)propionamide

A 50 g portion of (3S)-3-hydroxy-3-(2-thienyl)propionic acid ethyl ester obtained by the method of Example 3 (purity 95%) and 312.5 ml of 40% methylamine-methanol solution were charged into a one liter capacity flask and allowed to undergo the reaction at room temperature for 3.5 hours. Next, this was concentrated under a reduced pressure to obtain 45.96 g of crude crystals of (3S)-3-hydroxy-N-methyl-3-(2-thienyl)propionamide (yield 93%, purity 89%). A 9.16 g portion of the crude crystals was subjected to recrystallization with a toluene/methanol mixed solvent to obtain 6.69 g of purified (3S)-3-hydroxy-N-methyl-3-(2-thienyl)propionamide (purity 99%).

This chemical purity was determined by a high performance liquid chromatography under the following conditions.

MCI-Gel ODS 15 cm (mfd. by Mitsubishi Kagaku) 40° C.

Acetonitrile: 50 mM ammonium acetate aqueous solution=50:50 (0.4 ml/min)

Detection wavelength UV 230 nm

Also, its optical purity was determined by a high performance liquid chromatography under the following conditions to find that it was 99.9% ee.

Chiral CD-Ph (mfd. by Shiseido) 30° C.

Acetonitrile: 0.1 M $NaClO_4$ aqueous solution=20:80 (0.3 ml/min)

Detection wavelength UV 230 nm

Figure 4:
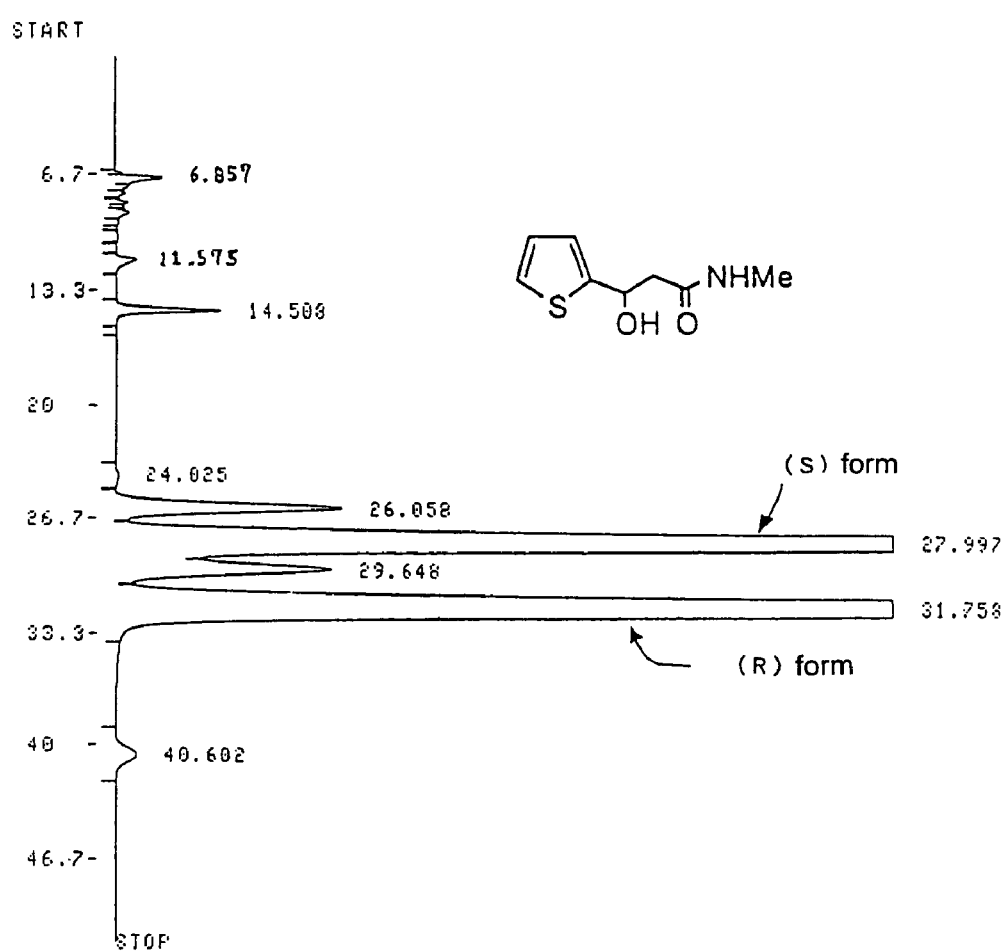
FIG. 4 is a chart showing a result of the HPLC analysis of racemic bodies of 3-hydroxy-N-methyl-3-(2-thienyl)propionamide. The retention time (minute) is plotted as abscissa.
Figure 5:
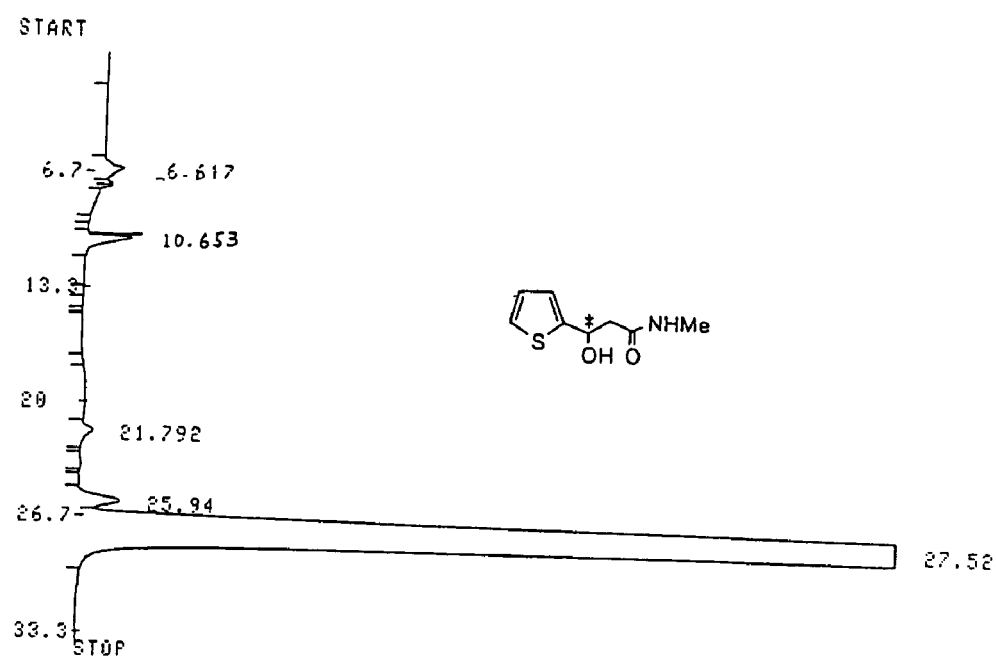
FIG. 5 is a chart showing a result of the HPLC analysis of (S)-form 3-hydroxy-N-methyl-3-(2-thienyl)propionamide obtained by the amidation of (S)-form 3-hydroxy-3-(2-thienyl)propionic acid ethyl ester formed by an asymmetric reduction reaction.

In addition, racemic bodies of 3-hydroxy-N-methyl-3-(2-thienyl)propionamide obtained by the amidation of the racemic bodies of 3-hydroxy-3-(2-thienyl)propionic acid ethyl ester obtained as standard preparations in the aforementioned Example 3 were used as the standards to carry out the analysis under the aforementioned conditions, and by analyzing optical rotatory power of the thus obtained two peaks (peaks having retention times of 28 minutes and 32 minutes in FIG. 4), peaks of (R)-form (retention time 32 minutes in FIG. 4) and (S)-form of 3-hydroxy-N-methyl-3-(2-thienyl)propionamide (retention time 28 minutes in FIG. 4) were identified. When the crystals obtained in this Example 4 was analyzed, it was confirmed that a peak was formed at the same detection time of (3S)-3-hydroxy-N-methyl-3-(2-thienyl)propionamide.

Figure 6:
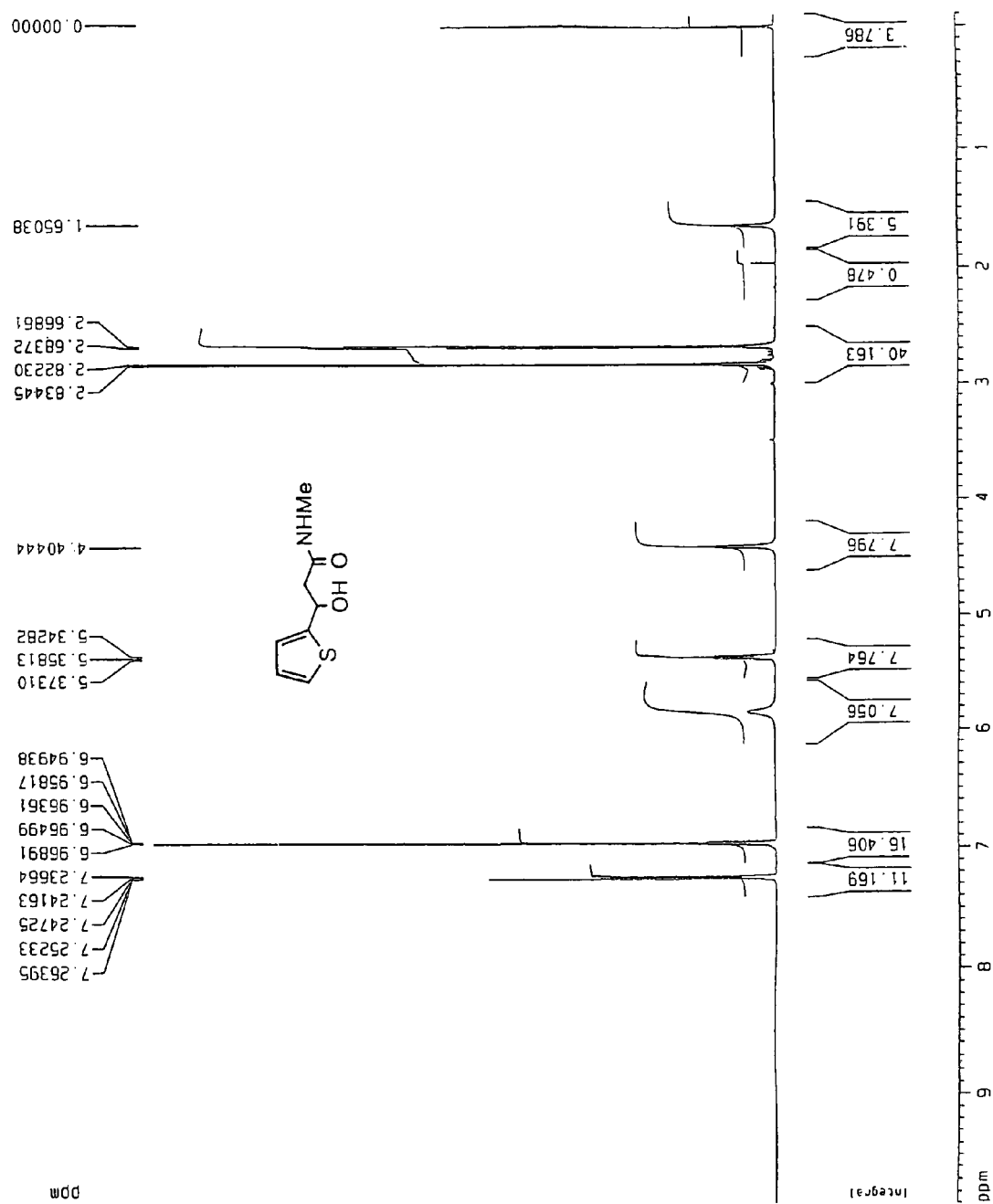
FIG. 6 is a chart showing a result of the NMR analysis of (S)-form 3-hydroxy-N-methyl-3-(2-thienyl)propionamide obtained by the amidation of (S)-form 3-hydroxy-3-(2-thienyl)propionic acid ethyl ester formed by an asymmetric reduction reaction.

Also, it was analyzed by NMR that the crystals obtained by this Example 4 are of 3-hydroxy-N-methyl-3-(2-thienyl)propionamide (FIG. 6).

$^1$H-NMR ($CDCl_3$) δ 2.67 (d, 2H, J=6 Hz), 2.82, 2.83 (s, 3H, rotational isomer derived from methylamido group), 4.40 (br, 1H), 5.36 (t, 1H, J=6 Hz), 5.75–5.90 (br, 1H), 6.92–6.98 (m, 1H), 7.22–7.26 (m, 2H)

Example 5

Synthesis of (3S)-3-hydroxy-N-methyl-3-(2-thienyl)propionamide

A 10 ml-capacity flask was charged with 1.10 g (10.9 mmol) of triethylamine and 0.2 ml of dry DMF, next, 0.50 g (10.9 mmol) of formic acid and 7 mg (0.01 mmol) of RuCl (p-cymene) (SS-TsDPEN) was added thereto under ice-cooling, and 0.20 g (1.09 mmol) of the N-methyl-3-oxo-3-(2-thienyl)propionamide obtained in Production Example 5 was finally added thereto, and the mixture was stirred at 40° C. for 10 hours. After the reaction, this was adjusted to pH 1 by adding 5% hydrochloric acid, extracted with ethyl acetate and washed with saturated brine, the solvent was concentrated under a reduced pressure and then the residue was purified by a silica gel column chromatography to obtain 0.16 g of (3S)-3-hydroxy-N-methyl-3-(2-thienyl)propionamide (yield 80%).

In addition, its optical purity was determined by the same method as in the aforementioned Example 4 to find that it was 97.0% ee.

Example 6

Synthesis of (3S)-3-hydroxy-N-methyl-3-(2-thienyl)propionamide

A 24.2 g portion of crude (3S)-3-hydroxy-3-(2-thienyl)propionic acid ethyl ester (purity 97.7% by weight, 97.5% ee) obtained in accordance with Example 1, excepting for not carrying out the chromatographic purification, was dissolved in 48 ml of methanol, and this was mixed with 27.5 g of 40% methylamine-methanol solution at room temperature and stirred overnight at room temperature. Next, the contents were concentrated to 57 g under a reduced pressure, mixed with 220 ml of toluene, and then the resulting contents were concentrated to 197 g at a solution temperature of 70° C. Thereafter, this solution was gradually cooled to 25° C. to effect crystallization, and the resulting crystals were collected by filtration, washed with 30 ml of toluene and then dried under a reduced pressure to obtain 19.5 g of (3S)-3-hydroxy-N-methyl-3-(2-thienyl)propionamide (yield 88%).

In addition, its optical purity was determined by the same method as in Example 4 to find that it was 100% ee.

Example 7

Reduction of Amide Using Aluminum Reducing Agent

A 500 ml capacity flask was charged with 13 g of (3S)-3-hydroxy-N-methyl-3-(2-thienyl)propionamide obtained in Example 6 (100% ee) and 65 ml of toluene, 60.8 g of Red-Al toluene solution adjusted to 49% was added dropwise thereto at a solution temperature of from 45 to 60° C. This was further stirred at a solution temperature of from 50 to 55° C. for 4 hours, 63 ml of saturated brine was added dropwise thereto at the same temperature, the insoluble matter was removed by Celite (trade name) filtration, and then the filtrate was separated between layers and the organic layer was concentrated to 62.5 g under a reduced pressure. Thereafter, the precipitated inorganic salts were removed by filtration, the resulting filtrate was concentrated to 36 g under a reduced pressure and cooled to 20° C. to effect crystallization, and then the thus formed crystals were mixed with 70 ml of n-heptane to carry out 0.5 hour of aging at 5° C., collected by filtration, washed with n-heptane and diisopropyl ether and dried under a reduced pressure to obtain 8.4 g of (3S)-3-methylamino-1-(2-thienyl)-1-propanol (yield 70%).

Its chemical purity was determined by a high performance liquid chromatography under the following conditions to find that it was 100%.

L-column (mfd. by Sugiyama Shoji) 40° C.
Acetonitrile: 50 mM ammonium acetate aqueous solution=30:70 (0.6 ml/min)
Detection wavelength UV 230 nm Also, its optical purity was determined by a high performance liquid chromatography under the following conditions to find that it was 100% ee.

Chiral CD-Ph (mfd. by Shiseido) 35° C.
Acetonitrile: 0.1 M $NaClO_4$ aqueous solution=40:60 (0.5 ml/min)
Detection wavelength UV 230 nm $^1$H-NMR ($CDCl_3$, 400 MHz) δ 1.93 (m, 2H), 2.44 (s, 3H), 2.80 (m, 2H), 5.15 (td, 1H, J=3 Hz, 8 Hz), 6.95 (m, 2H), 7.21 (d, 1H, J=6.2 Hz)

Example 8

Reduction of Amide Using Aluminum Reducing Agent

A 200 ml capacity flask was charged with 5.00 g of (3S)-3-hydroxy-N-methyl-3-(2-thienyl)propionamide (optical purity >99.5% ee) and 26 ml of toluene. A 18.3 g portion of 75% by weight toluene solution of sodium bis(2-methoxyethoxy)aluminum hydride was adjusted to 50% by weight by diluting with toluene and added dropwise to the reaction solution at 50° C. spending 10 minutes and stirred for 2 hours. The reaction solution was cooled down to room temperature and mixed with 30 ml of 11% sodium hydroxide aqueous solution, and then the organic layer and water layer were separated. The water layer was extracted twice with 10 ml of toluene, the organic layers were combined, and then 404 mg of L-(+)-tartaric acid and 10 ml of saturated brine were added thereto and stirred for 20 minutes. The mixed solution was separated between layers and then the organic layer was concentrated to obtain 4.27 g of a brown oily substance. When the amount of aluminum contained in this oily substance was measured by the ICP-AES determination method, it was 5 ppm or less. This oily substance was dissolved in 30 ml of toluene, mixed with 0.3 g of activated carbon and stirred for 30 minutes, and then the activated carbon was removed by filtration. The solution was concentrated, mixed with 7 ml of toluene and stirred at room temperature, and then the thus formed pale yellow crystals were collected by filtration, washed with 4 ml of toluene and dried under a reduced pressure to obtain 1.88 g of (1S)-3-methylamino-1-(2-thienyl)-1-propanol (yield 41%).

When chemical purity and optical purity of this compound were determined in the same manner as in Example 6, the chemical purity was 100% and the optical purity was >99.5% ee, respectively.

In addition, when the amount of aluminum contained in the crystals was measured, it was 5 ppm or less.

Purification Example 1

A 100 mg portion of pale yellow crystals of (1S)-3-methylamino-1-(2-thienyl)-1-propanol (optical purity >99.5% ee) having an aluminum content of 230 ppm was dissolved in 3 ml of water, mixed with 18 mg of L-(+)-tartaric acid and stirred at room temperature. The reaction solution was mixed with a few drops of 25% sodium hydroxide aqueous solution and sodium chloride and extracted twice with 10 ml of toluene. The organic layer was concentrated to recover 97 mg of pale yellow crystals (optical purity >99.5% ee). When the amount of aluminum contained in the crystals was measured in the same manner as in Example 8, it was 5 ppm or less.

Purification Example 2

A 100 mg portion of pale yellow crystals of (1S)-3-methylamino-1-(2-thienyl)-1-propanol (optical purity >99.5% ee) having an aluminum content of 230 ppm was dissolved in 3 ml of water, mixed with 22 mg of disodium dihydrogen ethylenediaminetetraacetate and stirred at room temperature. The reaction solution was mixed with a few drops of 25% sodium hydroxide aqueous solution and sodium chloride and extracted twice with 10 ml of toluene. The organic layer was concentrated to recover 98 mg of pale yellow crystals (optical purity >99.5% ee). When the amount of aluminum contained in the crystals was measured in the same manner as in Example 8, it was 5 ppm or less.

Example 9

Reduction of Amide Using Boron Reducing Agent

A flask equipped with a condenser was charged with (3S)-3-hydroxy-N-methyl-3-(2-thienyl)propionamide (optical purity >99.5% ee, 1.50 g, 8.1 mmol), 97% sodium borohydride (0.735 g, 19.4 mmol) and tetrahydrofuran (9.9 ml), a tetrahydrofuran (5.1 ml) solution of iodine (2.06 g, 8.1 mmol) was slowly added dropwise thereto at room temperature spending 20 minutes, and then the mixture after completion of the dropwise addition was heated under reflux for 4 hours. After completion of the reaction, the reaction solution was ice-cooled, mixed with 2-butanone (7.5 ml) and 1 N sodium hydroxide aqueous solution (30 ml), heated at a solution temperature of 64° C. for 20 minutes and then analyzed by a liquid chromatography under the same conditions of Example 7, thereby finding that conversion ratio of the material was 99%, and yield of the product of interest (1S)-3-methylamino-1-(2-thienyl)-1-propanol was 91% (optical purity >99.5% ee).

Example 10

Reduction of Amide Using Boron Reducing Agent

A 316.2 ml portion of 1.03 M $BH_3$ tetrahydrofuran solution (2 molar equivalents of the substrate) was put into a 2 liter capacity flask and ice-cooled. Next, 31.44 g of (3S)-3-hydroxy-N-methyl-3-(2-thienyl)propionamide (purity 95.9, >99.9% ee) was dissolved in 235.8 ml of tetrahydrofuran and slowly added dropwise thereto in such a manner that the solution temperature became 2 to 5° C. Next, by increasing the temperature, heating reflux was carried out for 3 hours. The reaction was monitored by a liquid chromatography under the same conditions of Example 7, and after completion of the reaction, ice-cooling was carried out and 628.8 ml of water was slowly added dropwise thereto in such a manner that the solution temperature became 15° C. or less. The pH value of the reaction solution at this stage was 9. Further continuously, 9.81 g of acetic acid was added thereto under ice-cooling. The pH value after completion of the addition was 5.

After stirring for about 15 minutes, the pH was adjusted to about 8 with 25% NaOH aqueous solution for the purpose of removing by-products, and then the solvent was replaced by 551 ml of toluene and the water layer was extracted twice with 551 ml of toluene.

In this connection, when the pH value at this stage is too high, the product of interest is also extracted in a large amount together with the by-products, so that it is desirable to carry out the extraction after adjusting within the range of generally from pH 6.5 to 9, preferably from pH 7 to 8.5.

After further adjusting the water layer after extraction to approximately pH 11 by adding 28% aqueous ammonia, the product of interest was extracted using ethyl acetate, dried and concentrated to obtain 17.4 g of (1S)-3-methylamino-1-(2-thienyl)-1-propanol (>99.9% ee).

In general, it is desirable to carry out this step after elimination of by-products at about pH 11, because higher liquid pH is desirable for efficiently extracting the product of interest.

$^1$H-NMR (CDCl$_3$, 400 MHz) δ 1.93 (m, 2H), 2.44 (s, 3H), 2.80 (m, 2H), 5.15 (td, 1H, J=3 Hz, 8 Hz), 6.95 (m, 2H), 7.21 (d, 1H, J=6.2 Hz)

Reference Example 2

When 0.05 g of (1S)-3-methylamino-1-(2-thienyl)-1-propanol (97% ee) was dissolved in 1 ml of tetrahydrofuran to which 35% hydrochloric acid was added at 20° C. (pH in the system=about 1) and stirred for 30 minutes, its optical purity was 75% ee.

Reference Example 3

When 0.05 g of (1S)-3-methylamino-1-(2-thienyl)-1-propanol (97% ee) was dissolved in 1 ml of tetrahydrofuran to which acetic acid was added at 20° C. (pH in the system=about 3) and stirred for 48 hours, its optical purity was 95% ee.

Reference Example 4

When 0.05 g of (1S)-3-methylamino-1-(2-thienyl)-1-propanol (96.6% ee) was dissolved in 1 ml of tetrahydrofuran to which a buffer solution of pH=4.0 was added at 20° C. and stirred for 48 hours, its optical purity was 96.6% ee.

Though the invention has been described in detail and with reference to specific embodiments, it is evident to those skilled in the art that many variations and modifications can be applied thereto without departing from the spirit and scope of the invention.

This application is based on the Japanese patent application filed on Mar. 19, 2002 (Japanese Patent Application No. 2002-076168), Japanese patent application filed on Apr. 30, 2002 (Japanese Patent Application No. 2002-129140), Japanese patent application filed on May 16, 2002 (Japanese Patent Application No. 2002-141145), Japanese patent application filed on Aug. 5, 2002 (Japanese Patent Application No. 2002-227401), Japanese patent application filed on Aug. 5, 2002 (Japanese Patent Application No. 2002-227402), Japanese patent application filed on Aug. 6, 2002 (Japanese Patent Application No. 2002-228495), Japanese patent application filed on Sep. 13, 2002 (Japanese Patent Application No. 2002-267617), and Japanese patent application filed on Oct. 31, 2002 (Japanese Patent Application No. 2002-317857), and the contents thereof are incorporated herein by references.

INDUSTRIAL APPLICABILITY

A thiophene ring-containing optically active alcohol can be obtained with high yield and high optical yield by the method of the invention.

The invention claimed is:

1. A method for producing a 3-hydroxy-3-(2-thienyl)propionamide represented by formula (1):

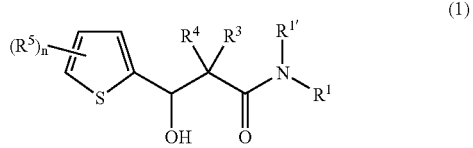

(1)

wherein
R$^1$ and R$^{1'}$ each independently represents a hydrogen atom, an alkyl group, an aryl group or an aralkyl group,
R$^3$ and R$^4$ each independently represents a hydrogen atom or an alkyl group, wherein R$^3$ and R$^4$ may together form a carbon ring,
R$^5$ represents a halogen atom, a nitro group, a hydroxyl group, an alkyl group which may be substituted, an aryl group which may be substituted or an alkoxy group which may be substituted, and
n is an integer of from 0 to 3, comprising:
subjecting a β-ketocarbonyl compound represented by formula (3):

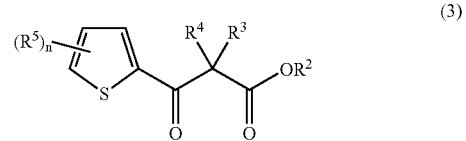

(3)

wherein R$^1$, R$^{1'}$, R$^3$, R$^4$, R$^5$ and n are as defined above, and R$^2$ is represents an alkyl group, an aryl group or an aralkyl group, to an asymmetric reduction using a cell, a treated product of said cell and/or a culture medium of a microorganism having the ability to stereoselectively reduce carbonyl group, and then the resulting product is allowed to react with an amine represented by the formula $R^1R^{1'}NH$, wherein $R^1$ and $R^{1'}$ are as defined above, to effect its amidation.

2. The method of claim 1, wherein the microorganism having the ability to stereoselectively reduce carbonyl group is a microorganism selected from the group consisting of the genus *Ambroziozyma*, the genus *Arthrobacter*, the genus *Brettanomyces*, the genus *Brevibacterium*, the genus *Bullera*, the genus *Candida*, the genus *Citeromyces*, the genus *Corynebacterium*, the genus *Cryptococcus*, the genus *Cystofilobasidium*, the genus *Debaryomyces*, the genus *Dekkera*, the genus *Endomyces*, the genus *Exophiala*, the genus *Fellomyces*, the genus *Filobasidium*, the genus *Hanseniaspora*, the genus *Holtermannia*, the genus *Issatchenkia*, the genus *Kloeckera*, the genus *Kluyveromyces*, the genus *Kodamaea*, the genus *Komagataella*, the genus *Leucosporidium*, the genus *Lipomyces*, the genus *Lodderomyces*, the genus *Metschnikowia*, the genus *Ogataea*, the genus *Paenibacillus*, the genus *Pichia*, the genus *Rhodotorula*, the genus *Saccharomyces*, the genus *Saccharomycopsis*, the genus *Saitoella*, the genus *Shizosaccharomyces*, the genus *Sirobasidium*, the genus *Sporidiobolus*, the genus *Sterigmatomyces*, the genus *Sterigmatosporidium*, the genus *Torulaspora*, the genus *Tremella*, the genus *Trichosporon*, the genus *Trichosporonoides*, the genus *Trigonopsis*, the genus *Waltomyces*, the genus *Wickerhamiella*, the genus *Williopsis*, the genus *Yamadazyma* and the genus *Yarrowia*.

3. The method of claim 1, wherein the microorganism having the ability to stereoselectively reduce carbonyl group is a microorganism selected from the group consisting of the genus *Arthrobacter*, the genus *Candida*, the genus *Cryptococcus*, the genus *Kloeckela*, the genus *Kodamaea*, the genus *Leucosporidium*, the genus *Metschnikowia*, the genus *Paenibacillus*, the genus *Pichia* and the genus *Saccharomyces*.

4. The production method according to claim 1, wherein the microorganism having the ability to stereoselectively reduce carbonyl group is a microorganism selected from the group consisting of the genus *Ambroziozyma*, the genus *Arthrobacter*, the genus *Brettanomyces*, the genus *Brevibacterium*, the genus *Bullera*, the genus *Candida*, the genus *Citeromyces*, the genus *Corynebacterium*, the genus *Cryptococcus*, the genus *Cystofilobasidium*, the genus *Debaryomyces*, the genus *Dekkera*, the genus *Endomyces*, the genus *Exophiala*, the genus *Fellomyces*, the genus *Filobasidium*, the genus *Hanseniaspora*, the genus *Holtermannia*, the genus *Issatchenkia*, the genus *Kloeckera*, the genus *Kluyveromyces*, the genus *Komagataella*, the genus *Lipomyces*, the genus *Lodderomyces*, the genus *Metschnikowia*, the genus *Ogataea*, the genus *Rhodotorula*, the genus *Saccharomyces*, the genus *Saccharomycopsis*, the genus *Saitoella*, the genus *Shizosaccharomyces*, the genus *Sirobasidium*, the genus *Sporidiobolus*, the genus *Sterigmatomyces*, the genus *Sterigmatosporidium*, the genus *Torulaspora*, the genus *Tremella*, the genus *Trichosporon*, the genus *Trichosporonoides*, the genus *Trigonopsis*, the genus *Waltomyces*, the genus *Wickerhamiella*, the genus *Williopsis*, the genus *Yamadazyma* and the genus *Yarrowia*.

5. The method of claim 1, wherein the β-ketocarbonyl compound represented by formula (3) is reduced using a cell.

6. The method of claim 1, wherein the β-ketocarbonyl compound represented by formula (3) is reduced using a treated product of a cell.

7. The method of claim 1, wherein the β-ketocarbonyl compound represented by formula (3) is reduced using a culture medium of a microorganism having the ability to stereoselectively reduce a carbonyl group.

* * * * *